US006293954B1

(12) United States Patent
Fogarty et al.

(10) Patent No.: US 6,293,954 B1
(45) Date of Patent: Sep. 25, 2001

(54) SURGICAL CLAMP WITH REPLACEABLE CLAMP MEMBERS

(75) Inventors: Thomas J. Fogarty, Portola Valley; Thomas A. Howell; David Willis, both of Palo Alto, all of CA (US)

(73) Assignee: Novare Surgical Systems, Inc., Cupertino, CA (US)

( * ) Notice: Subject to any disclaimer, the term of this patent is extended or adjusted under 35 U.S.C. 154(b) by 0 days.

(21) Appl. No.: 09/337,119

(22) Filed: Jun. 21, 1999

(51) Int. Cl.$^7$ .................................................... A61B 17/08
(52) U.S. Cl. ........................... 606/151; 606/205; 606/207
(58) Field of Search ................................. 606/151, 157, 606/158, 205–207

(56) References Cited

U.S. PATENT DOCUMENTS

| | | |
|---|---|---|
| 1,048,937 | 12/1912 | Brightwell . |
| 2,743,726 | 5/1956 | Grieshaber . |
| 3,746,002 | 7/1973 | Haller . |
| 3,779,248 | 12/1973 | Karman ................................. 128/321 |
| 3,880,166 | 4/1975 | Fogarty . |
| 3,993,076 | 11/1976 | Fogarty . |
| 4,286,598 * | 9/1981 | Kapitanov ............................. 606/207 |
| 4,612,708 | 9/1986 | Hattori ................................... 30/260 |
| 4,768,687 | 9/1988 | Ault ...................................... 223/116 |
| 4,821,719 | 4/1989 | Fogarty . |
| 5,057,016 * | 10/1991 | Lukase ................................. 433/159 |
| 5,279,416 | 1/1994 | Malec et al. ......................... 206/339 |
| 5,308,358 | 5/1994 | Bond et al. .......................... 606/205 |
| 5,529,571 | 6/1996 | Daniel ................................... 600/219 |
| 5,569,274 | 10/1996 | Rapacki et al. ...................... 606/158 |
| 5,582,615 | 12/1996 | Foshee et al. ....................... 606/139 |
| 5,591,182 | 1/1997 | Johnson ............................... 606/151 |
| 5,643,307 * | 7/1997 | Turkel et al. ........................ 606/114 |
| 5,810,865 | 9/1998 | Koscher et al. ..................... 606/174 |
| 5,810,881 | 9/1998 | Hoskin et al. ....................... 606/207 |
| 5,893,876 * | 4/1999 | Turkel et al. ........................ 606/205 |

FOREIGN PATENT DOCUMENTS

| | | | |
|---|---|---|---|
| WO 89/06939 | 8/1989 | (WO) | ....................................... 17/56 |
| WO 95/15723 | 6/1995 | (WO) | ....................................... 17/32 |

* cited by examiner

*Primary Examiner*—Gary Jackson
(74) *Attorney, Agent, or Firm*—Morrison & Foerster LLP

(57) ABSTRACT

A jaw-type surgical clamp having replaceable clamp members is disclosed. The jaws are pivotally movable and include telescoping attachment portions and anti-rotation surfaces. The clamp members connect to the attachment portions and include anti-rotation surfaces that engage the anti-rotation surfaces of the jaws to prevent rotation. Mutually engagable structures releasably lock the jaws and the clamp members together.

35 Claims, 15 Drawing Sheets

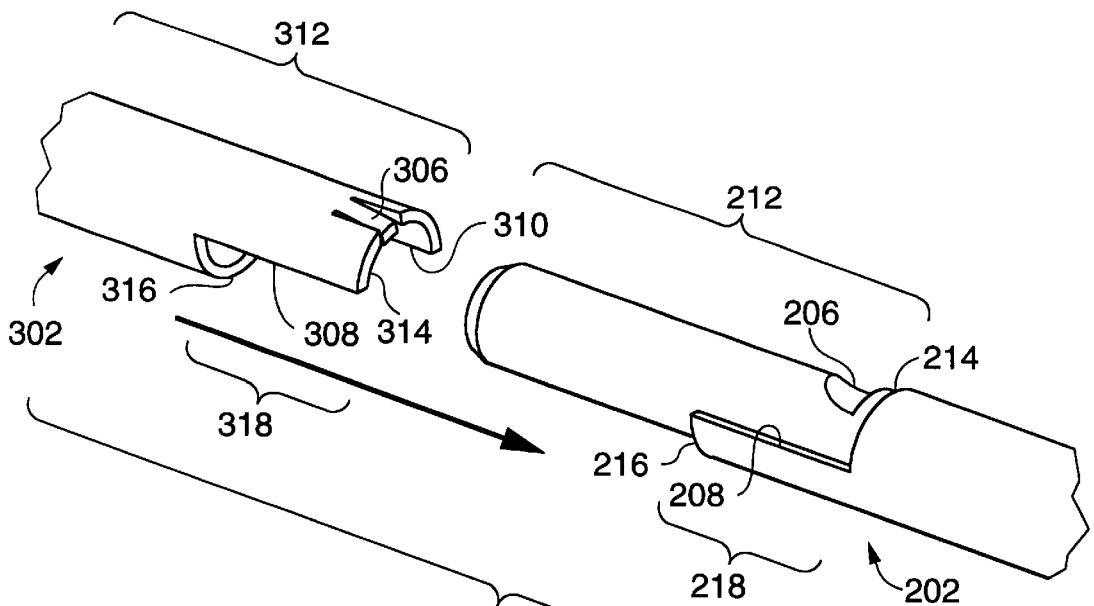
FIG. 4
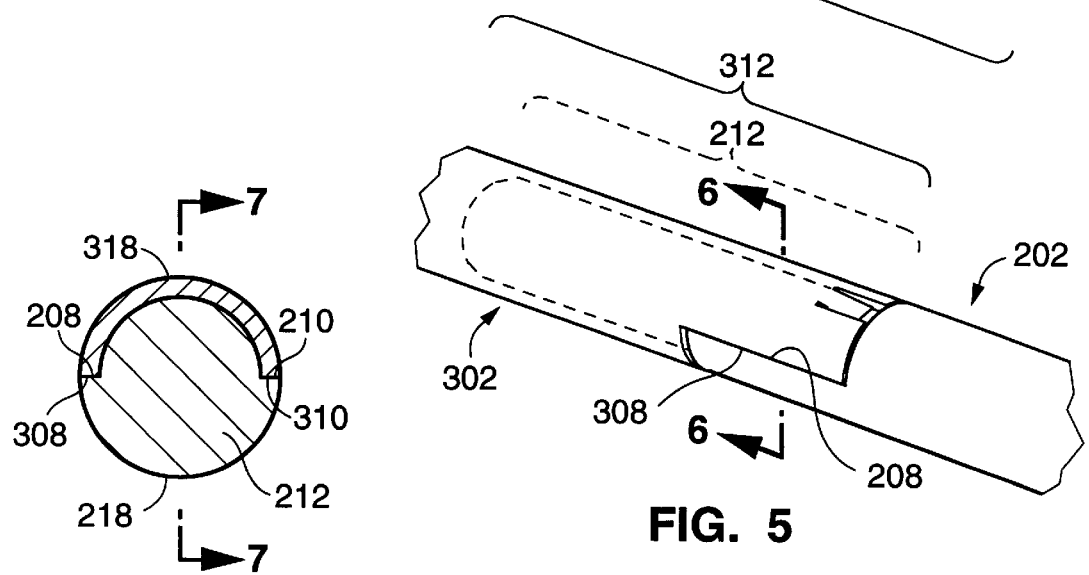
FIG. 6
FIG. 5
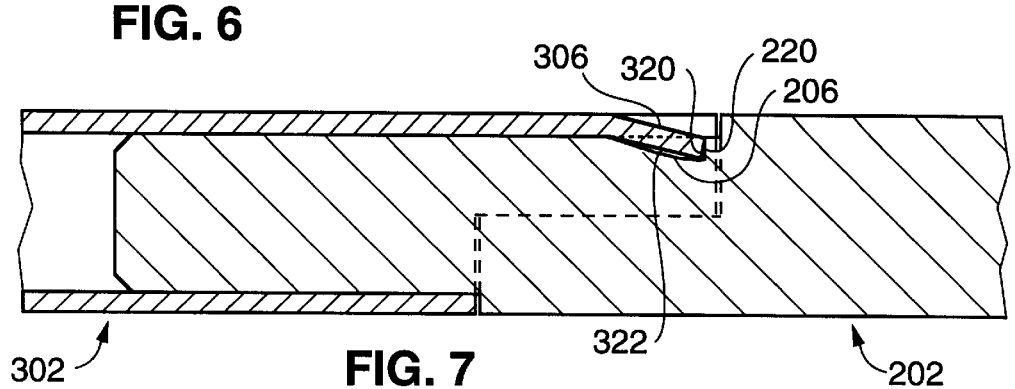
FIG. 7

FIG. 6A  FIG. 5A

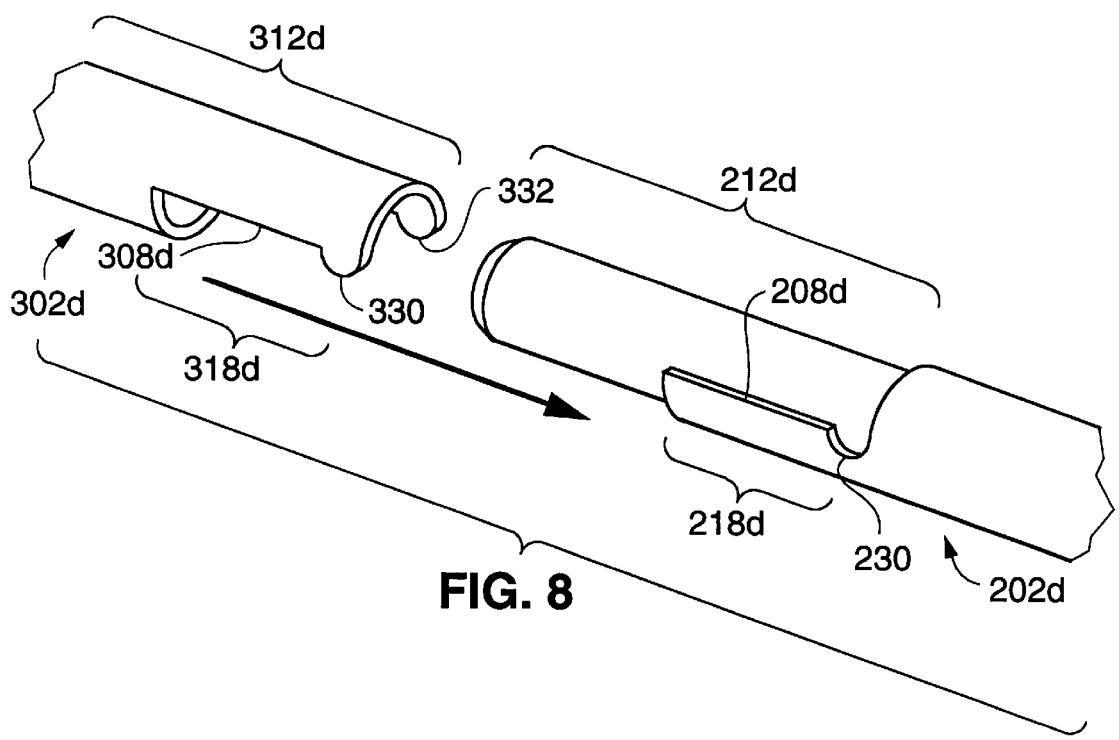
FIG. 8
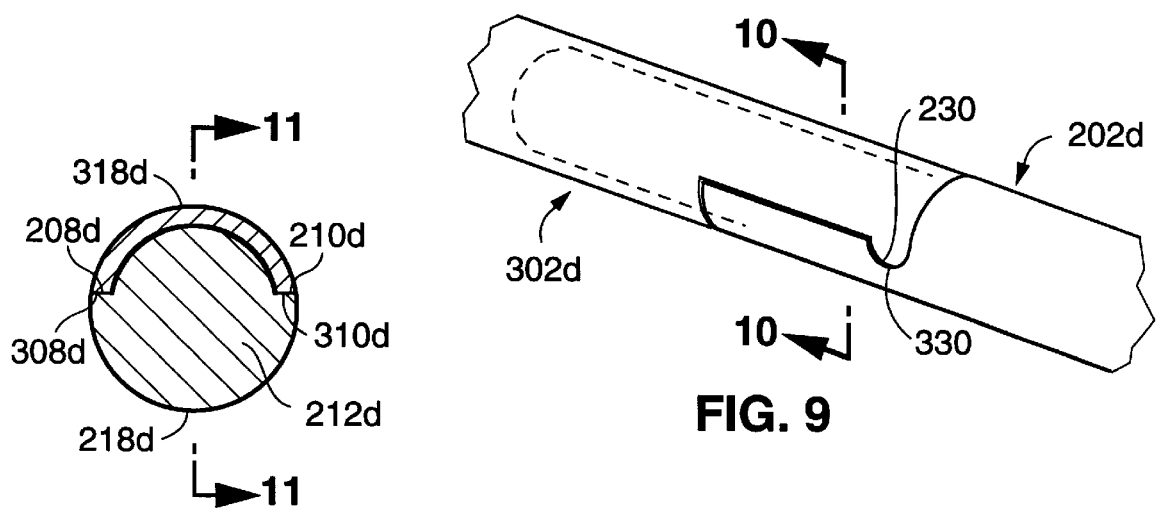
FIG. 10
FIG. 9
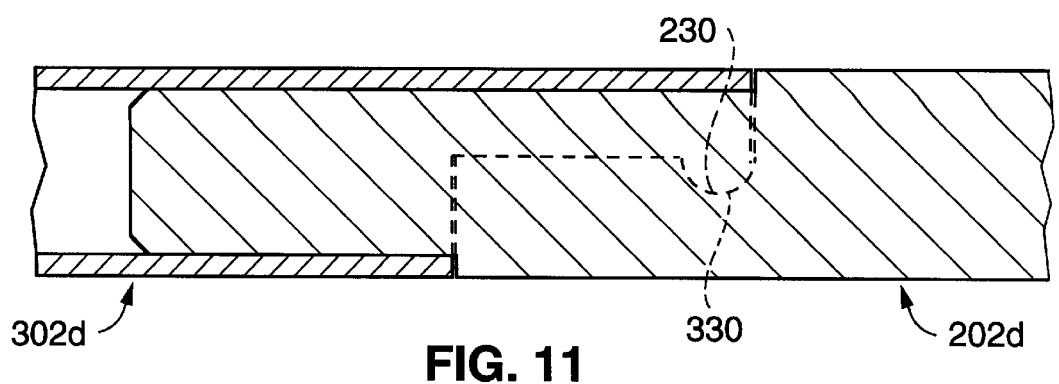
FIG. 11

SURGICAL CLAMP WITH REPLACEABLE CLAMP MEMBERS

BACKGROUND OF THE INVENTION

The present invention relates to surgical clamps. In particular, the invention relates to surgical clamps having removable clamping members.

A wide variety of surgical clamps exist in order to perform a correspondingly wide variety of functions. Typically, however, a separate clamp must be purchased for each desired clamp functional surface, clamp size, and clamp shape.

One potential solution would be to change the pads on the clamp. U.S. Pat. No. 4,821,719 discloses a surgical clamp with replaceable pads. Similarly, U.S. Pat. No. 2,743,726 discloses a surgical clamp with a detachable resilient sleeve. The replaceable pads and resilient sleeve conform to the existing clamp functional surface. Thus, they do not allow different clamp functional surfaces, sizes, or shapes, making this an imperfect solution.

Another potential solution would be to provide a removable clamping structure. U.S. Pat. No. 5,569,274 discloses an endoscopic device with a releasable clamp. The releasable clamp allows multiple clamp surfaces to be first attached and then released. It is not, however, designed to provide for manipulation of the object clamped after clamping has occurred.

U.S. Pat. No. 5,582,615 discloses a hemostatic clip applicator with a removable surgical instrument. The surgical instrument disclosed is a clip applicator. It does not show that this concept can be applied to surgical clamps.

U.S. Pat. No. 5,308,358 discloses a shafted surgical instrument with a detachable shaft yoke. The shaft yoke is detachable for cleaning purposes. It fails to show that the actuators at the end of the shaft are themselves detachable, and does not suggest that the actuators can form clamping surfaces. Thus, it does not disclose a way of providing multiple clamping surfaces.

A final potential solution is disclosed in U.S. Pat. No. 1,048,937, which describes a wrench with detachable jaws. There is no teaching, however, that this innovation can be applied to other arts, such as the art of surgical tools. Furthermore, it shows that the jaws grip to perform turning, whereas the present invention grips to perform compression. Given that there is no need to use this wrench to compress pipes, a compression function appears to be an unnecessary application in an unrelated art, as compared to the art of surgical tools.

Thus, the problems that remain after consideration of the art include a need for multiple clamping surfaces at low cost, the manipulation of the object clamped after clamping has occurred, and compression of the object clamped.

SUMMARY OF THE INVENTION

The present invention addresses these and other problems of the prior art by providing a jaw-type surgical clamp with removable clamp members. This allows replacement of the clamp members on the jaw. In addition, it allows multiple styles of clamp members to be used with a single handle portion. This can reduce the acquisition cost of an assortment of surgical clamps by requiring the purchase of only one handle portion. In addition, it allows compression of a clamped object. Finally, it allows the surgical clamp to manipulate a clamped object because the clamp members do not rotate with respect to the jaw.

According to one embodiment, a jaw-type surgical clamp includes a pair of jaws, a pair of clamp members, and mutually engagable structures which releasably lock the clamp members and jaws. The jaws are movable toward and away from each other. The jaws have an attachment portion and an anti-rotation surface. The clamp members are removably attachable to the jaws and have an attachment portion and an anti-rotation surface. The attachment portion of the clamp is configured to telescopically engage the attachment portion of the jaw. The anti-rotation surface of the clamp is configured to complementarily engage the anti-rotation surface of the jaw to prevent rotation between the clamp and the jaw.

According to another embodiment, a jaw-type surgical clamp kit includes the elements described above with the addition of a plurality of pairs of clamp members. Each pair of the plurality has a different clamping surface.

A principal object of the invention is to provide a surgical clamp wherein the clamp members are removably attachable.

Another object of the invention is to provide a surgical clamp wherein multiple clamping surfaces, shapes and cross-sections are available without requiring a user to purchase multiple surgical clamps.

Still another object is to provide a surgical clamp wherein a clamped object can be manipulated with the clamp after the object has been clamped.

A further object of the invention is to provide an improved surgical clamp with replaceable clamping members which are locked against rotation relative the handle members of the clamp.

Yet another object is to provide a surgical clamp that allows compression of the clamped object.

These and other objects will become apparent when viewed in light of the following detailed description and accompanying drawings.

BRIEF DESCRIPTION OF THE DRAWINGS

FIG. 4 is an enlarged exploded perspective view, with parts thereof broken away, of a part of the first embodiment of the surgical clamp shown in FIG. 1;

FIG. 5 is an enlarged perspective view, with parts thereof broken away, of the structures of FIG. 4 in an engaged condition;

FIG. 5A is an enlarged perspective view, with parts thereof broken away, of the structures of FIG. 4A in an engaged condition;

FIG. 6 is a cross-sectional view taken on the plane designated by line 6—6 of FIG. 5;

FIG. 6A is a cross-sectional view taken on the plane designated by line 6A—6A of FIG. 5A;

FIG. 7 is a cross-sectional view taken on the plane designated by line 7—7 of FIG. 6, showing the detent structures in an engaged condition;

FIG. 8 is an enlarged exploded perspective view, with parts thereof broken away, of a jaw-type surgical clamp according to a second embodiment of the present invention;

FIG. 9 is an enlarged perspective view, with parts thereof broken away, of the structures of FIG. 8 in an engaged condition;

FIG. 10 is a cross-sectional view taken on the plane designated by line 10—10 of FIG. 9;

FIG. 11 is a cross-sectional view taken on the plane designated by line 11—11 of FIG. 10, showing the detent structures in an engaged condition;

DETAILED DESCRIPTION OF THE PREFERRED EMBODIMENTS

First Embodiment

Figure 1:
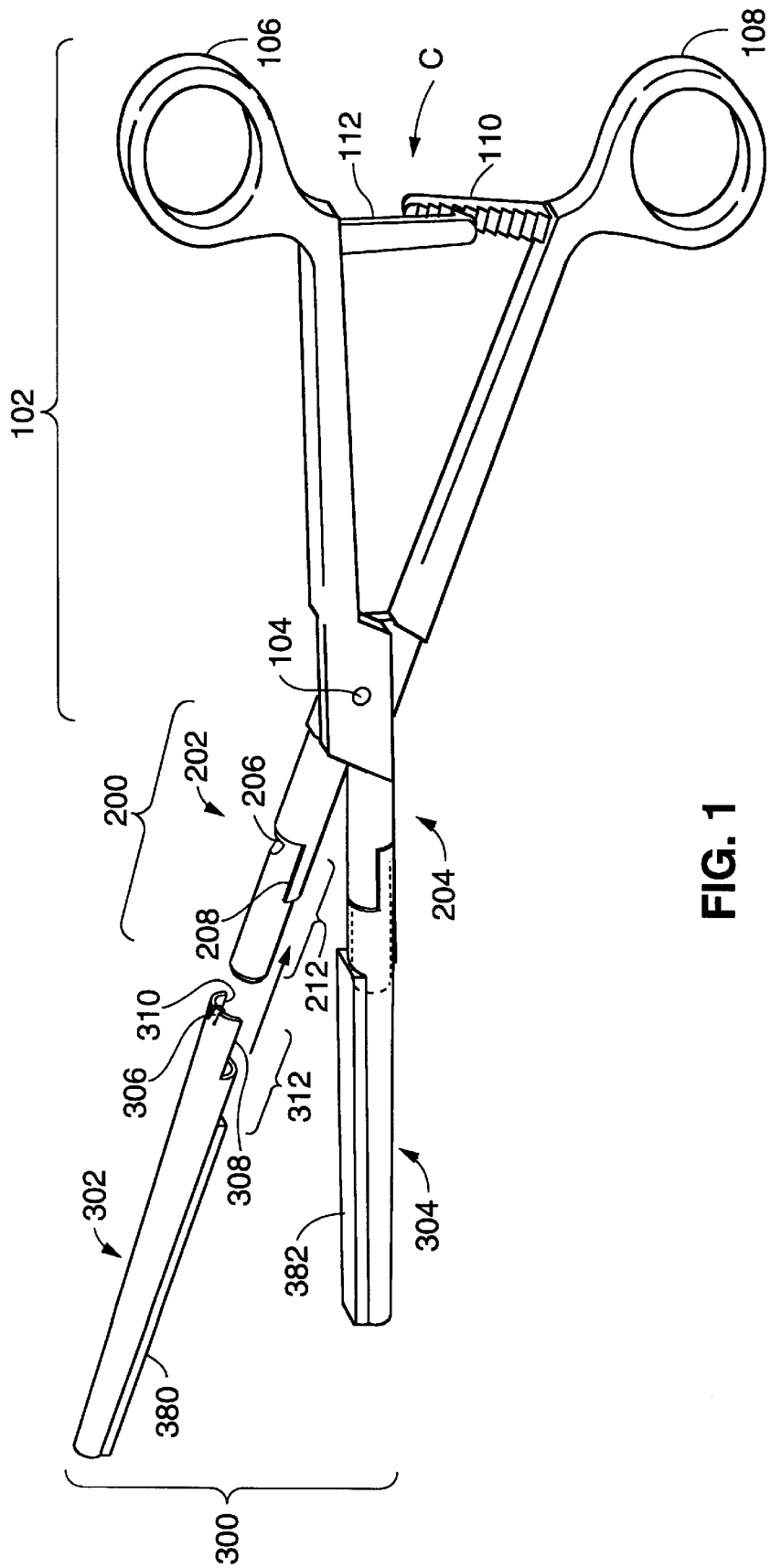
FIG. 1 is a perspective view of a jaw-type surgical clamp according to a first embodiment of the present invention.

This embodiment is shown in FIG. 1. The clamp of this embodiment, designated in its entirety by the letter C, comprises a handle portion 102, a jaw portion 200, and a clamp portion 300. Handle portion 102 includes most of the features of standard surgical clamps, including a pivot pin 104, handle rings 106 and 108, locking teeth 110, and locking notch 112. Handle portion 102 is made of stainless steel and is approximately 13 cm long. In another embodiment, handle portion 102 is fabricated with powdered metal. Handle portion 102 can be other sizes, shapes, or cross-sections suitable for hand operation.

Jaw portion 200 includes jaws 202 and 204, which are moveable toward and away from each other by operation of the pivot joint. Jaws 202 and 204 each include a notch 206, anti-rotation surfaces 208 and 210, and an attachment portion 212.

Clamp portion 300 includes clamp members 302 and 304, which are removably attachable to jaws 202 and 204. In FIG. 1, clamp member 302 is shown disconnected from jaw 202, and clamp member 304 is shown connected to jaw 204. Clamp members 302 and 304 may be made of any suitable material such as stainless steel, anodized aluminum, or powdered metal.

Clamp members 302 and 304 each include a detent tab 306, anti-rotation surfaces 308 and 310 (see FIG. 6), and an attachment portion 312. The attachment portion of the clamp members has an inner surface larger than an outer surface of the attachment portion 212 of the jaws, allowing attachment portion 312 to telescopically engage attachment portion 212.

Clamp members 302 and 304 include traction cushions 380 and 382. When both clamp members 302 and 304 are connected to jaws 202 and 204, traction cushions 380 and 382 form clamping surfaces when jaws 202 and 204 are moved toward each other. Cushions 380 and 382 are attached to clamp members 302 and 304, may be made of any suitable material, such as rubber, and include molded traction elements. The cushion material chosen will depend on the physical characteristics desired. The cushions may be attached to the clamp members by an adhesive, by bonding, or by integral fabrication.

Alternatively, the clamp members may be fabricated without traction cushions, and would instead have hard, cushionless surfaces.

Clamp members 302 and 304 are made of stainless steel and are about 65 mm long. The clamp members may also be made of injection-molded graphite-fiber reinforced polycarbonate, may be made of machined aluminum, may be molded in plastic, or may be fabricated with powdered metal.

Figure 1A:
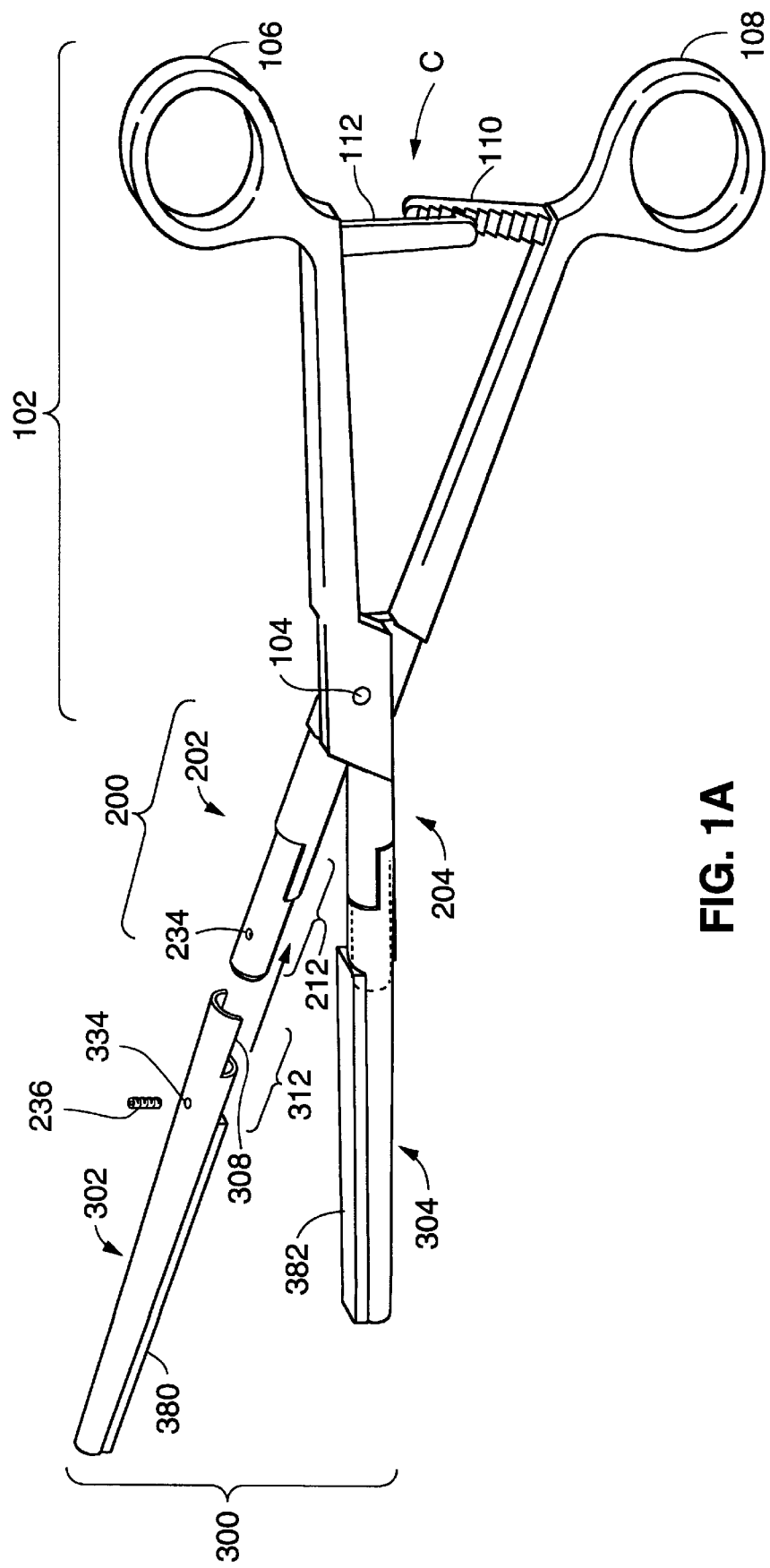
FIG. 1A is a perspective view of a jaw-type surgical clamp according to a modified first embodiment of the present invention.

FIG. 1A shows a modified first embodiment of clamp C that is presently a preferred embodiment. Elements of FIG. 1A corresponding to those of FIG. 1 are designated by like numerals. Clamp members 302 and 304 of FIG. 1A each include a hole 334 that passes completely through a tubular wall of the member. Hole 334 may be about 0.039 inches in diameter, or another suitable diameter to accommodate insertion of a wrench or screwdriver (not shown). Jaws 202 and 204 of the modified first embodiment each include a threaded bore 234 extending from the outer surface of the jaw into the interior. Set screw 236 may preferably be a #2:56 socket-head set screw. Bore 234 may be formed with #2:56 threads or another thread size suitable for interaction with hole 334 and set screw 236 (see FIGS. 6A and 7A and the accompanying text). Set screw 236 and bore 340 may be increased in size, for example to #4:40 threads, for larger surgical clamps.

Figure 2:
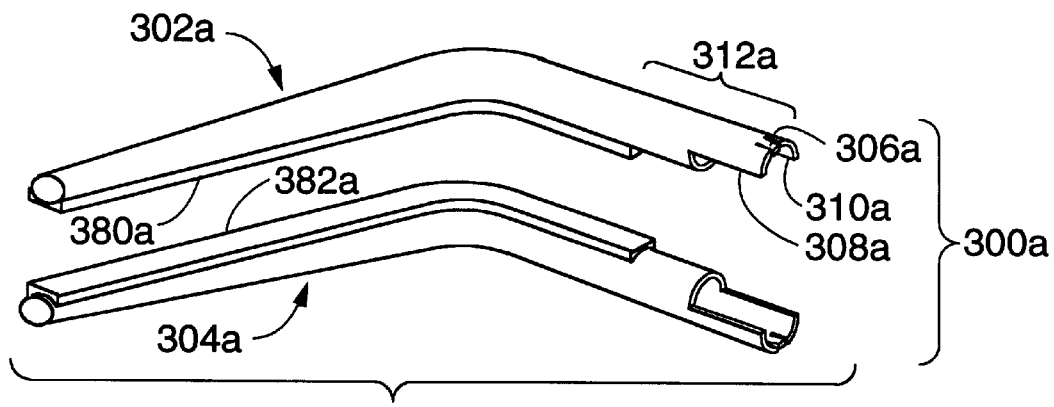
FIG. 2 is a perspective view of a second pair of clamp members of a second shape usable with the first embodiment of the surgical clamp shown in FIG. 1.
Figure 3:
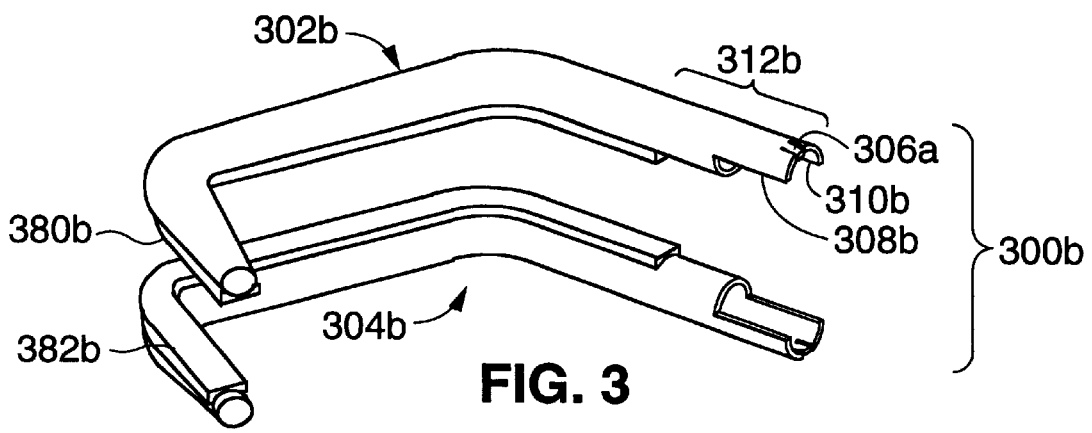
FIG. 3 is a perspective view of a third pair of clamp members of a third shape usable with the first embodiment of the surgical clamp shown in FIG. 1.

FIGS. 2 and 3 show other types of clamp portions attachable to jaw portion 200 in the same manner as clamp portion 300. FIG. 2 shows clamp portion 300a composed of clamp members 302a and 304a that are approximately 85 mm long and include one bend. Clamp members 302a and 304a include traction cushions 380a and 382a, detent tab 306a, anti-rotation surfaces 308a and 310a, and attachment portion 312a. FIG. 3 shows clamp portion 300b composed of clamp members 302b and 304b that are approximately 85 mm long and include two bends. Clamp members 302b and 304b include traction cushions 380b and 382b, detent tab 306b, anti-rotation surfaces 308b and 310b, and attachment portion 312b.

Many other sizes and configurations for the clamp members are possible. Suitable types of clamps, graspers, and other tools include the Lambert-Kay style, the Pean style, the Harken auricle clamp style, the Kelly tissue grasper style, and the Backhaus towel clamp style.

Figure 4A:
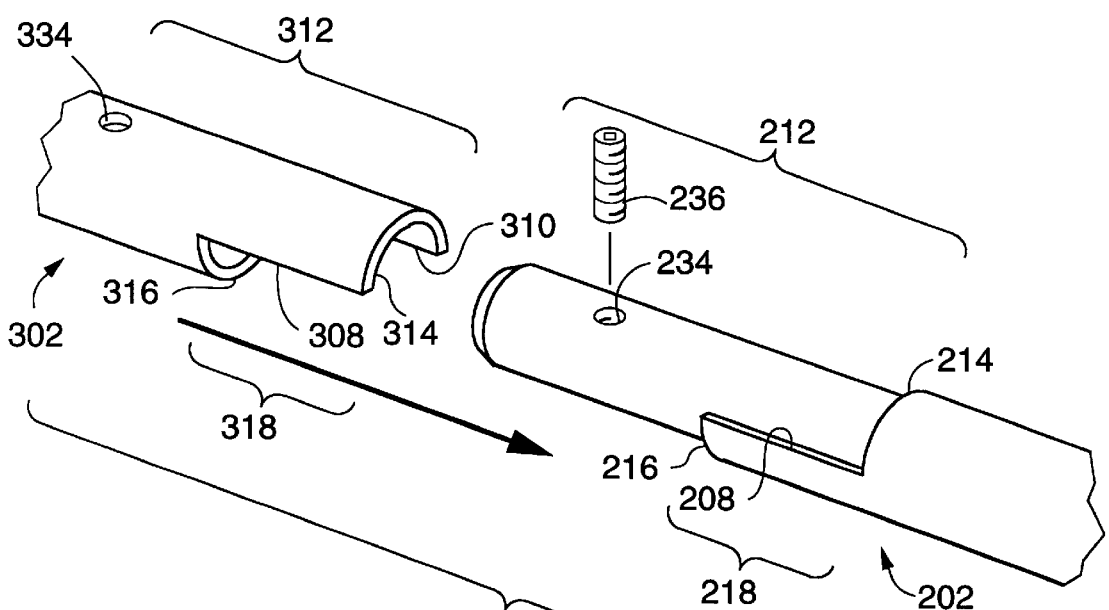
FIG. 4A is an enlarged exploded perspective view, with parts thereof broken away, of a part of the modified first embodiment of the surgical clamp shown in FIG. 1A.

FIGS. 4, 4A, and 5 illustrate a more detailed view of the attachment portions of the jaws and the clamp members shown in FIGS. 1 and 1A. FIG. 4 illustrates jaw 202 and clamp member 302 in a disengaged position, and FIG. 5 illustrates them in an engaged position. FIG. 4A illustrates jaw 202 and clamp member 302 in a disengaged position. As shown in FIG. 4, jaw 202 includes a first surface 214, a second surface 216, and a surrounding portion 218. Jaw 202 may be slightly beveled at its tip to facilitate alignment. Clamp member 302 includes a first surface 314, a second surface 316, and a surrounding portion 318.

FIG. 4A corresponds to FIG. 4 for the modified first embodiment, showing the addition of hole 334, set screw 236, and threaded bore 234, and the omission of tab 206 and notch 306.

As shown in FIG. 5, when attachment portion 312 slides onto attachment portion 212, numerous surfaces become mutually engaged: first surfaces 214 and 314, second surfaces 216 and 316, anti-rotation surfaces 208 and 308, and anti-rotation surfaces 210 and 310 (see FIG. 6). The engagement of surface 214 to 314 and surface 216 to 316 marks the termination of the telescopic engagement of clamp member 302 to jaw 202. The engagement of anti-rotation surface 208 to 308 and 210 to 310 prevents rotation of clamp member 302 around attachment portion 212.

FIG. 5A corresponds to FIG. 5 for the modified first embodiment shown in FIG. 1A. When clamp member 302 and jaw 202 are engaged, hole 334 lines up with threaded bore 234, providing access to set screw 236.

FIG. 6 shows that attachment portion 212 has a generally circular cross-section, allowing attachment portion 312 to rotate freely about a protruding portion of attachment portion 212 until clamp member 302 has been inserted sufficiently far for the anti-rotation surfaces to engage. The surrounding portions 218 and 318 each occupy about half of an outer surface of attachment portion 212.

FIG. 6A shows the interaction between hole 334, threaded bore 234, and set screw 236. When clamp member 302 and jaw 202 are engaged as shown in FIG. 5A, hole 334 allows access to set screw 236 in threaded bore 234. The set screw 236 engages the threads of bore 234. A screwdriver or hex wrench may be inserted into hole 334 to turn set screw 236, turning the screw and moving it inwardly (clockwise) or outwardly (counterclockwise). The screw 236 is moved inwardly to extend into the hole 334 into contact with the inner wall (lower surface) of attachment portion 312. This secures the clamp member 302 against separation from the jaw 202. The screw 234 is moved outwardly out of contact with the inner wall of attachment portion 312 to release the clamp member for separation from the jaw.

The set screw 236 may have a pointed or knurled tip for enhanced engagement with the inner wall of attachment portion 312. The hole 334 may be threaded slightly smaller than the threads of the screw 236 for tighter engagement, to prevent inadvertent loosening of the screw 236.

Preferably, the hole 334 has a diameter that permits insertion of the hex wrench but that is smaller than the diameter of the screw 236. This allows the screw to be turned outwardly, if desired, to contact the inner wall (upper surface) of attachment portion 312 to secure the clamp member 302.

Figure 7A:
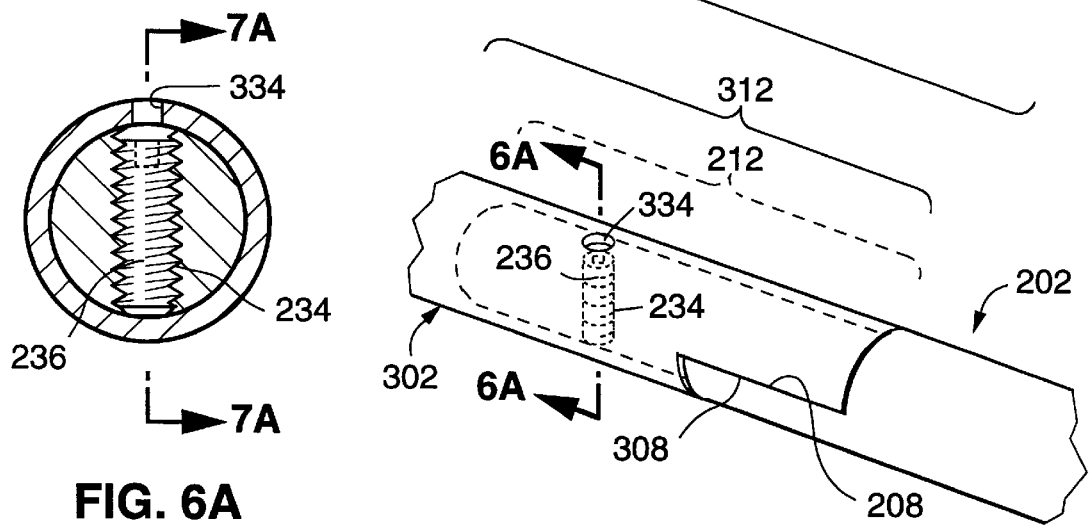
FIG. 7A is a cross-sectional view taken on the plane designated by line 7A—7A of FIG. 6A, showing the structures in an engaged condition.
Figure 7A:
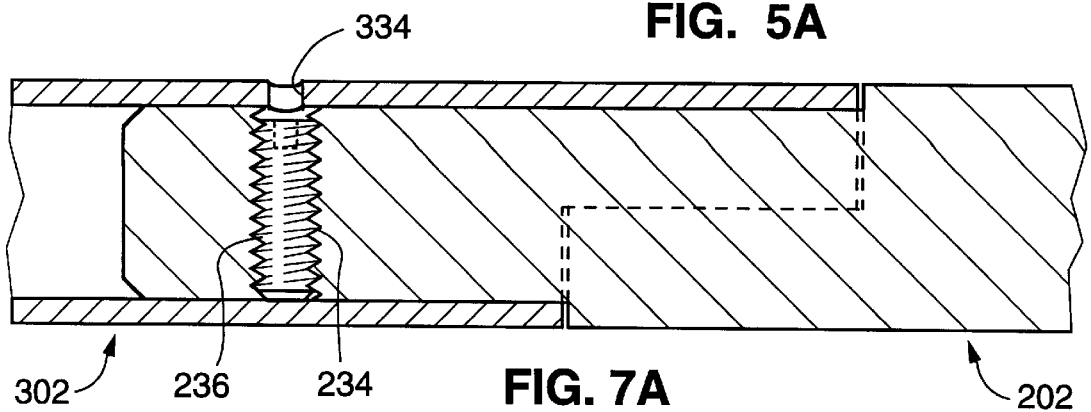

FIG. 7 shows an expanded view of the mutually engagable detent structures. Detent tab 306 is bent such that an outer corner 320 is flush with a top corner 220 of notch 206. Bottom surface 322 engages notch 206 to increase the removal resistance of clamp member 302.

FIG. 7A shows how set screw 236 locks the clamp member 302 against removal from the jaw 202 in the modified first embodiment. Screw 236 is in an intermediate position when the clamp member 302 is initially attached to the jaw 202. When screw 236 is turned to move inwardly, the tip the screw is positioned for engagement with the inner wall of attachment portion 312 to prevent removal of clamp member 302. To remove the clamp member 302, screw 236 is turned to move outwardly out of contact with the inner wall of attachment portion 312.

Second Embodiment

FIGS. 8 and 9 correspond to FIGS. 4 and 5 with other engagable detent structures according to a second embodiment of the surgical clamp. Clamp member 302d includes surrounding portion 318d, anti-rotation faces 308d and 310d (see FIG. 10), and notching segments 330 and 332. Jaw 202d includes attachment portion 212d, surrounding portion 218d, anti-rotation faces 208d and 210d (see FIG. 10), and notches 230 and 232 (opposite 230 and not shown in this view). Notch 230 engages notching segment 330, and notch 232 engages notching segment 332, to increase the removal resistance of clamp member 302d when engaged with attachment portion 212d.

FIG. 10 corresponds to FIG. 6 for the second embodiment of the surgical clamp as shown in FIG. 8. Attachment portion 212d has a generally circular cross-section, allowing attachment portion 312d to rotate freely about a protruding portion of attachment portion 212d until clamp member 302d has been inserted sufficiently far for the anti-rotation surfaces to engage. As before, anti-rotation surface 208d engages anti-rotation surface 308d, and anti-rotation surface 210d engages anti-rotation surface 310d. The surrounding portions 218d and 318d each occupy about half of an outer surface of the attachment portion 212d.

FIG. 11 corresponds to FIG. 7, showing a longitudinal cross-section of the detent structures of the second embodiment of the surgical clamp in an engaged condition.

Third Embodiment

Figure 12:
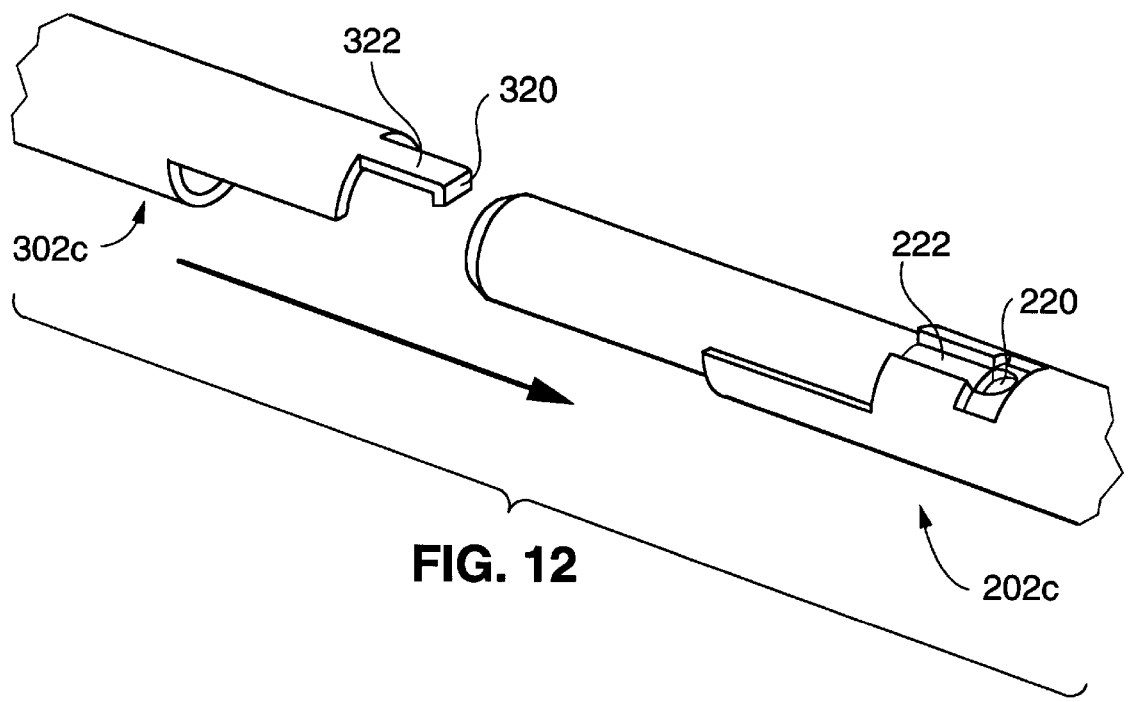
FIG. 12 is an enlarged exploded perspective view, with parts thereof broken away, of a jaw-type surgical clamp according to a third embodiment of the present invention.
Figure 13:
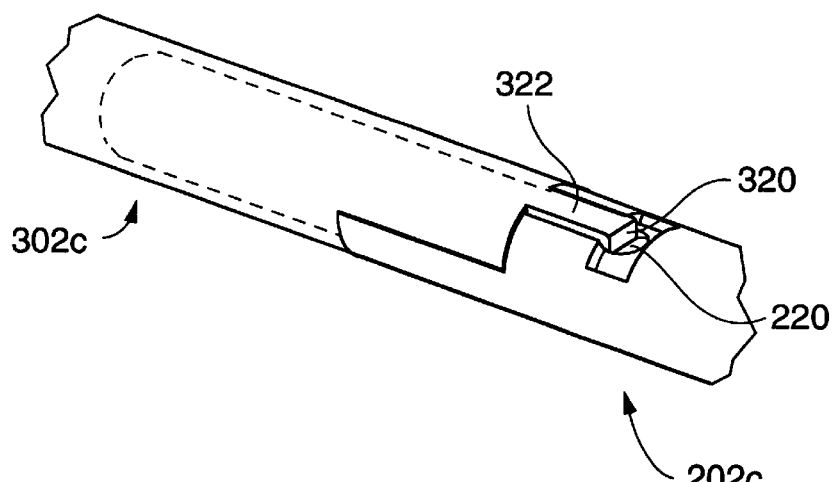
FIG. 13 is an enlarged perspective view, with parts thereof broken away, of the structures of FIG. 12 in an engaged condition.

FIGS. 12 and 13 correspond to FIGS. 4 and 5 with other engagable detent structures according to a third embodiment of the surgical clamp. Clamp member 302c includes an extended portion 322 and a bent portion 320. Jaw 202c includes a notch 220 and a groove 222. Notch 220 engages bent portion 320 to increase the removal resistance of the clamp member. Extended portion 322 engages groove 222 such that the sides of extended portion 322 engage the edges of the groove 222 to further resist rotation of the clamp member around the attachment portion of the jaw. Extended portion 322 has a resilience to enable the bent portion to slide over the groove 222 and snap into the notch 220.

Fourth Embodiment

Figure 14:
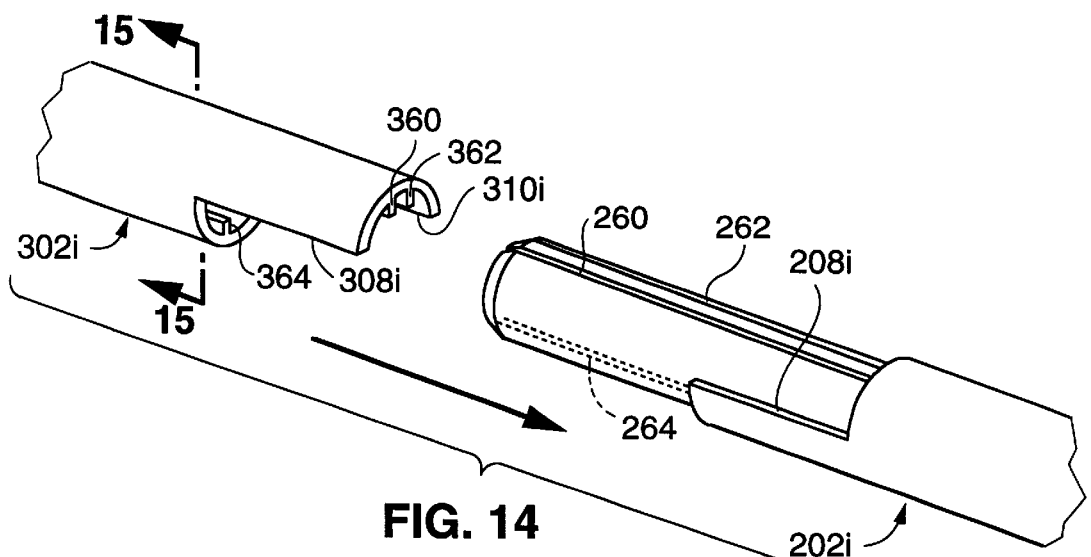
FIG. 14 is an enlarged exploded perspective view, with parts thereof broken away, of a jaw-type surgical clamp according to a fourth embodiment of the present invention.

FIG. 14 corresponds to FIG. 4 with other engagable detent structures according to a fourth embodiment of the surgical clamp. Jaw 202i has grooves 260, 262, and 264, and clamp member 302i has splines 360, 362, and 364. Splines 360, 362, and 364 fit into grooves 260, 262, and 264, respectively. When engaged, the splines and grooves prevent rotation between jaw 202i and clamp 302i and provide removal resistance. Note that anti-rotation surfaces 208i, 210i (not shown), 308i, and 310i are present and serve to supplement the rotation-preventing function of the splines and grooves.

Figure 15:
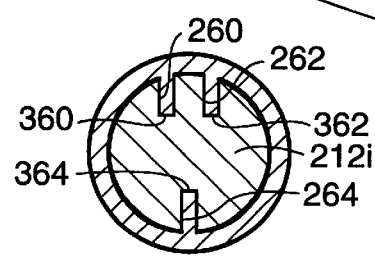
FIG. 15 is a cross-sectional view taken on the plane designated by line 15—15 of FIG. 14.

FIG. 15 corresponds to FIG. 6 for the fourth embodiment of the surgical clamp as shown in FIG. 14. Attachment portion 212i has a generally circular cross-section. When jaw 202i and clamp 302i are engaged, grooves 260, 262 and 264 engage splines 360, 362 and 364, respectively. Note that as shown in FIG. 15, the engaged grooves and splines prevent rotation between jaw 202i and clamp 302i.

Fifth Embodiment

Figure 30:
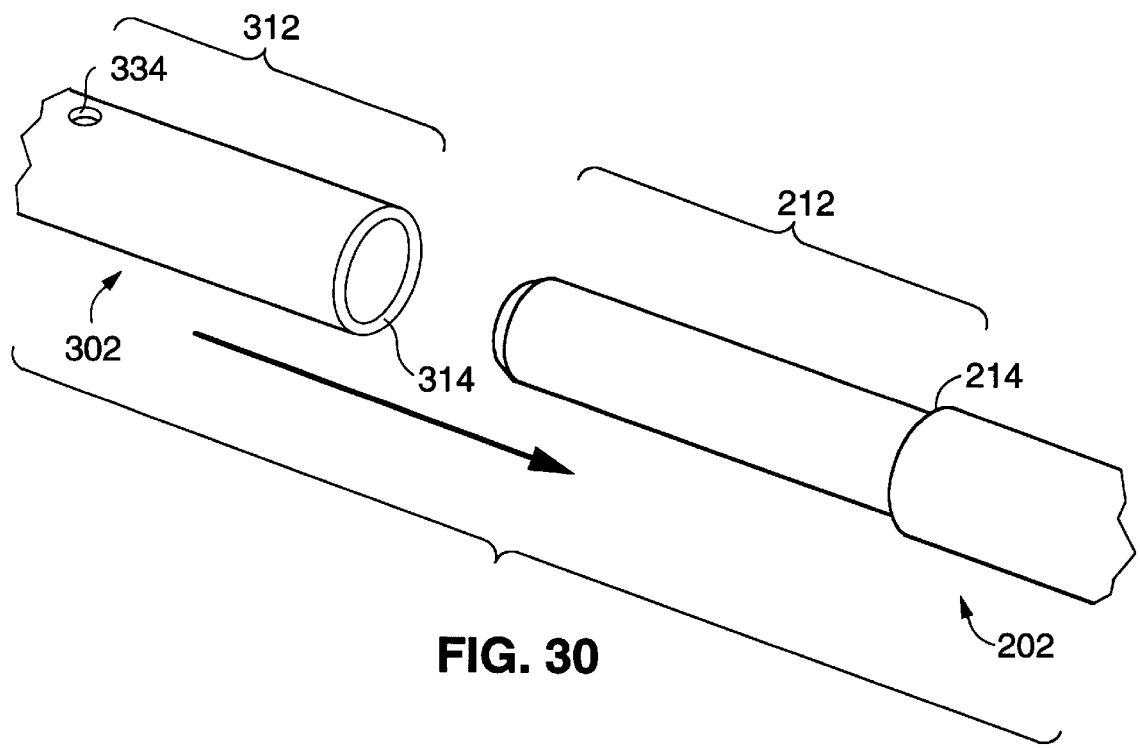
FIG. 30 is an enlarged exploded perspective view, with parts thereof broken away, of a jaw-type surgical clamp according to a fifth embodiment of the present invention.
Figure 31:
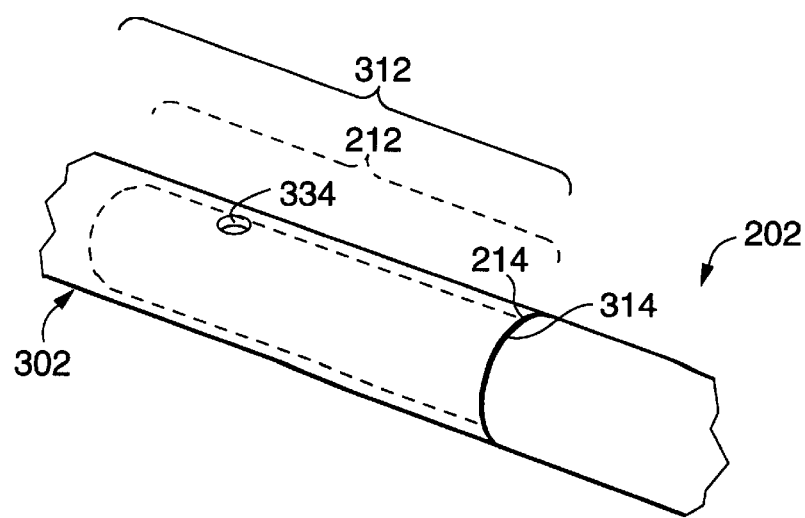
FIG. 31 is an enlarged perspective view, with parts thereof broken away, of the structures of FIG. 30 in an engaged condition.

FIGS. 30–31 correspond to FIGS. 4–5 and illustrate a fifth embodiment of the surgical clamp. In this embodiment, the clamp members are semi-permanently bonded to the jaws. As such, mutually engagable detent structures are not required. In addition, anti-rotation surfaces are not required because the bonding may be performed by the surgical clamp supplier, which can use alignment tools to correctly align the clamp members and the jaws.

The clamp members may be bonded with a metal brazing, a silver solder, or a glue, among other bonding materials. To bond the clamp member to the jaw, the parts may be attached as shown in FIG. 31, and the bonding substance may be applied where they connect at surfaces 214 and 314. The bonding substance then may flow between the attachment portions 212 and 312. The hole 334 is not required; however, hole 334 facilitates the bonding operation by allowing air to escape as the bonding substance flows in and by providing access to determine that the bonding substance has entered the attachment portions 212 and 312 at the location of the hole. The bonding substance then sets and bonds the clamp member to the jaw. The bonding is semi-permanent because the clamp member may be detached with an effort greater than that normally exerted by a user of the surgical clamp. It is envisioned that the removal would be performed by the clamp producer and not the user of the surgical clamp.

This embodiment is slightly less adaptable than the previous embodiments because the clamp members are semi-permanently bonded and are not as easily replaceable by the user as with the other embodiments. However, the semi-permanent bonding has a number of advantages for the surgical clamp producer. The producer may stock a few types of handles, and may bond the clamp members desired by a customer when an order is placed, instead of having to stock the handles that correspond to every type of clamp member. The customer may then return the surgical clamp to the producer and request the clamp members be replaced with another style of clamp members.

In addition, many vendors of surgical clamps produce either good clamp members or good handles, but not both. The present invention allows the clamp producer to select both good clamp members and good handles from two vendors and combine them in one surgical clamp.

Resilient Pad Structures

Figure 16:
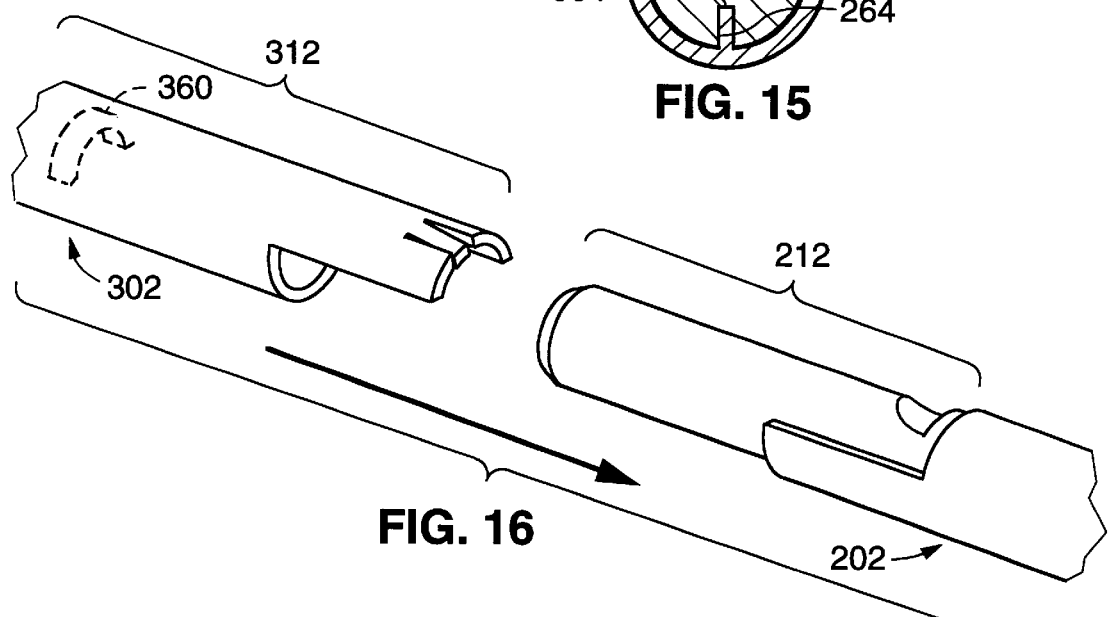
FIG. 16 is an enlarged exploded perspective view, with parts thereof broken away, of a first embodiment of a resilient insertion pad for use with the first, second, third, or fourth embodiments of the surgical clamp.

FIG. 16 corresponds to the first embodiment of the surgical clamp as shown in FIG. 4 with the addition of a resilient pad 360 within the attachment portion 312 of the clamp member 302. Pad 360 can be similarly positioned within the second, third, and fourth embodiments of the surgical clamp. Pad 360 is compressed by an end of the attachment portion 212 of jaw 202 when inserted into the attachment portion 312 of clamp member 302. Pad 360 has a shape of a semi-cylindrical surface, with a tapered edge to conform to the shape of the end of the attachment portion 212. Pad 360 resists relative insertion motion between clamp member 302 and jaw 202 and takes up play therebetween.

Figure 17:
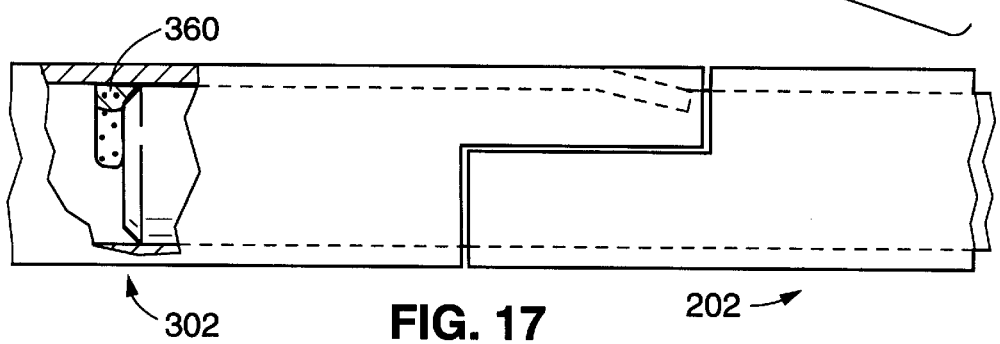
FIG. 17 is an enlarged perspective view, with parts thereof broken away, of the structures of FIG. 16 in an engaged condition.

FIG. 17 shows a side view of FIG. 16 with jaw 202 and clamp member 302 in an engaged condition. FIG. 17 corresponds to FIG. 7 with the addition of resilient pad 360.

Figure 18:
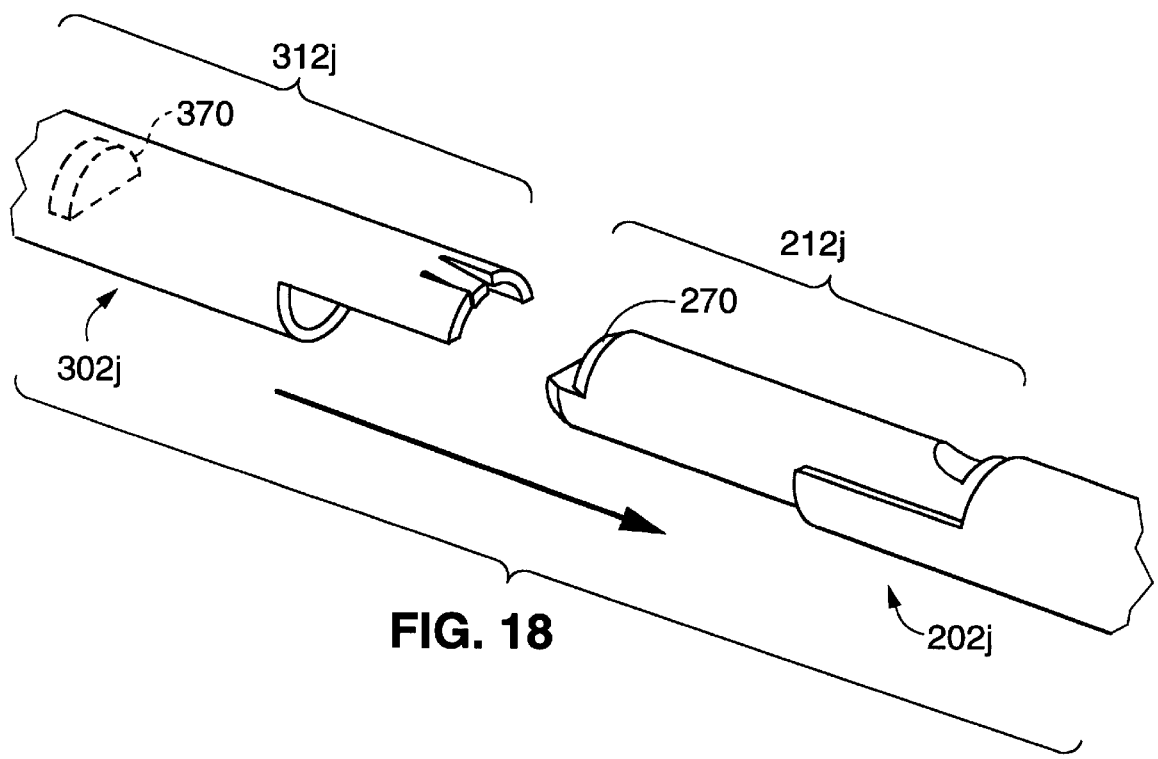
FIG. 18 is an enlarged exploded perspective view, with parts thereof broken away, of a second embodiment of a resilient insertion pad for use with the first, second, third, or fourth embodiments of the surgical clamp.

FIG. 18 shows a second embodiment of the resilient pad structure within the attachment portion 312j of the clamp member 302j, wherein the pad is designated 370. The resilient pad 370 can be similarly positioned within the first, second, third, and fourth embodiments of the surgical clamp. Pad 370 has a shape of a semi-cylinder. Jaw 202j includes a stepped end 270, a portion of which engages pad 370. Pad 370 functions similarly to the pad 360 and further resists relative motion between clamp member 302j and jaw 202j.

Figure 19:
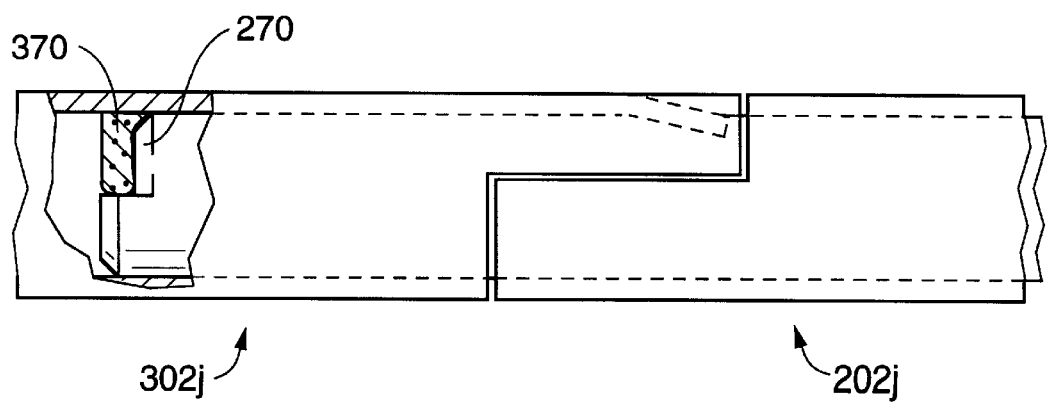
FIG. 19 is an enlarged perspective view, with parts thereof broken away, of the structures of FIG. 18 in an engaged condition.

FIG. 19 shows a side view of FIG. 18 with the jaw 202j and clamp member 302j in an engaged condition.

Alternative Cross-Sections

Figure 20:
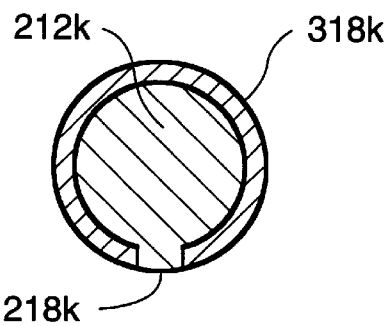
FIG. 20 is cross-sectional view of a first alternative placement of the anti-rotation faces.
Figure 21:
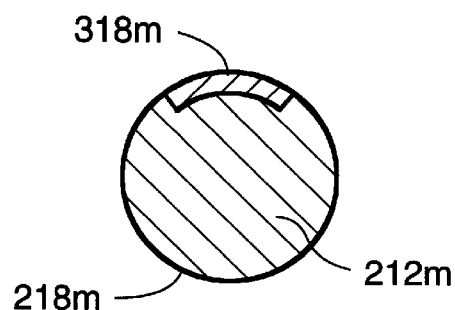
FIG. 21 is cross-sectional view of a second alternative placement of the anti-rotation faces.

FIGS. 20 and 21 correspond to FIG. 6 with other arrangements for the surrounding portions 218 and 318. In FIG. 20, the surrounding portion 318k of the clamp member occupies more than half of the outer surface of the attachment portion 212k, with the surrounding portion 218k of the jaw being correspondingly reduced. In FIG. 21, the surrounding portion 318m of the clamp member occupies less than half of the outer surface of the attachment portion 212m, with the surrounding portion 218m of the jaw being correspondingly reduced.

Figure 22:
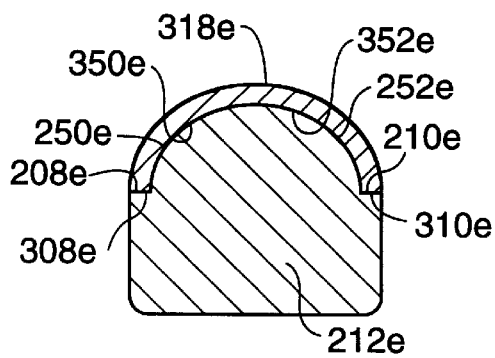
FIG. 22 is a cross-sectional view of a first alternative cross-section of the surgical clamp.

FIGS. 22–25 show other cross-sections of the attachment portion of the jaw, which correspond to and may be used in place of the cross-section of FIGS. 6 and 10. FIG. 22 shows a cross-section of attachment portion 212e of the jaw when engaged with protruding portion 318e of the clamp member. Anti-rotation surfaces 208e and 210e of the jaw engage anti-rotation surfaces 308e and 310e, respectively, of the clamp member. The cross-section shown in FIG. 22 is generally rectangular with a semi-ellipsoidal portion. Note that in addition to the rotation prevented by the anti-rotation surfaces, the non-circular cross-section also prevents rotation. Left-outer surface 250e engages left-inner surface 350e to prevent clockwise rotation. Similarly, right-outer surface 252e engages right-inner surface 352e to prevent counter-clockwise rotation.

Figure 23:
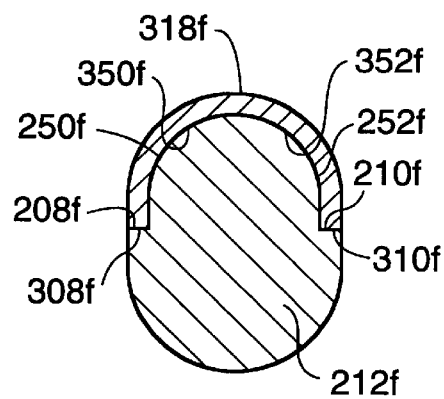
FIG. 23 is a cross-sectional view of a second alternative cross-section of the surgical clamp.

FIG. 23 shows an attachment portion with a generally ellipsoidal cross-section. Otherwise this figure corresponds to FIG. 22, with the letter "f" appended to each element number.

Figure 24:
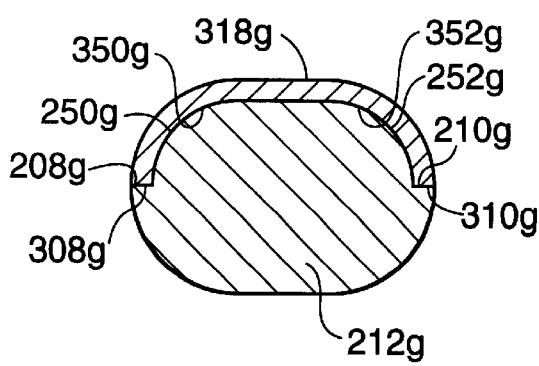
FIG. 24 is a cross-sectional view of a third alternative cross-section of the surgical clamp.

FIG. 24 shows an attachment portion with a generally ellipsoidal cross-section, with a long axis in the horizontal direction. Otherwise this figure corresponds to FIG. 22, with the letter "g" appended to each element number.

Figure 25:
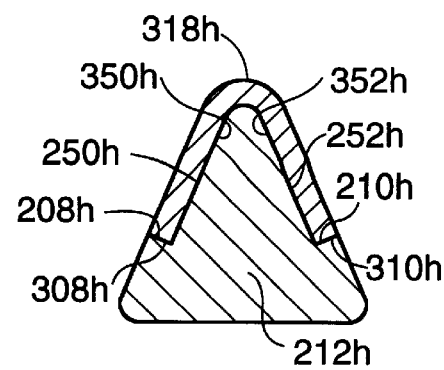
FIG. 25 is a cross-sectional view of a fourth alternative cross-section of the surgical clamp.

FIG. 25 shows an attachment portion with a generally triangular cross-section. Otherwise this figure corresponds to FIG. 22, with the letter "h" appended to each element number.

Figure 26:
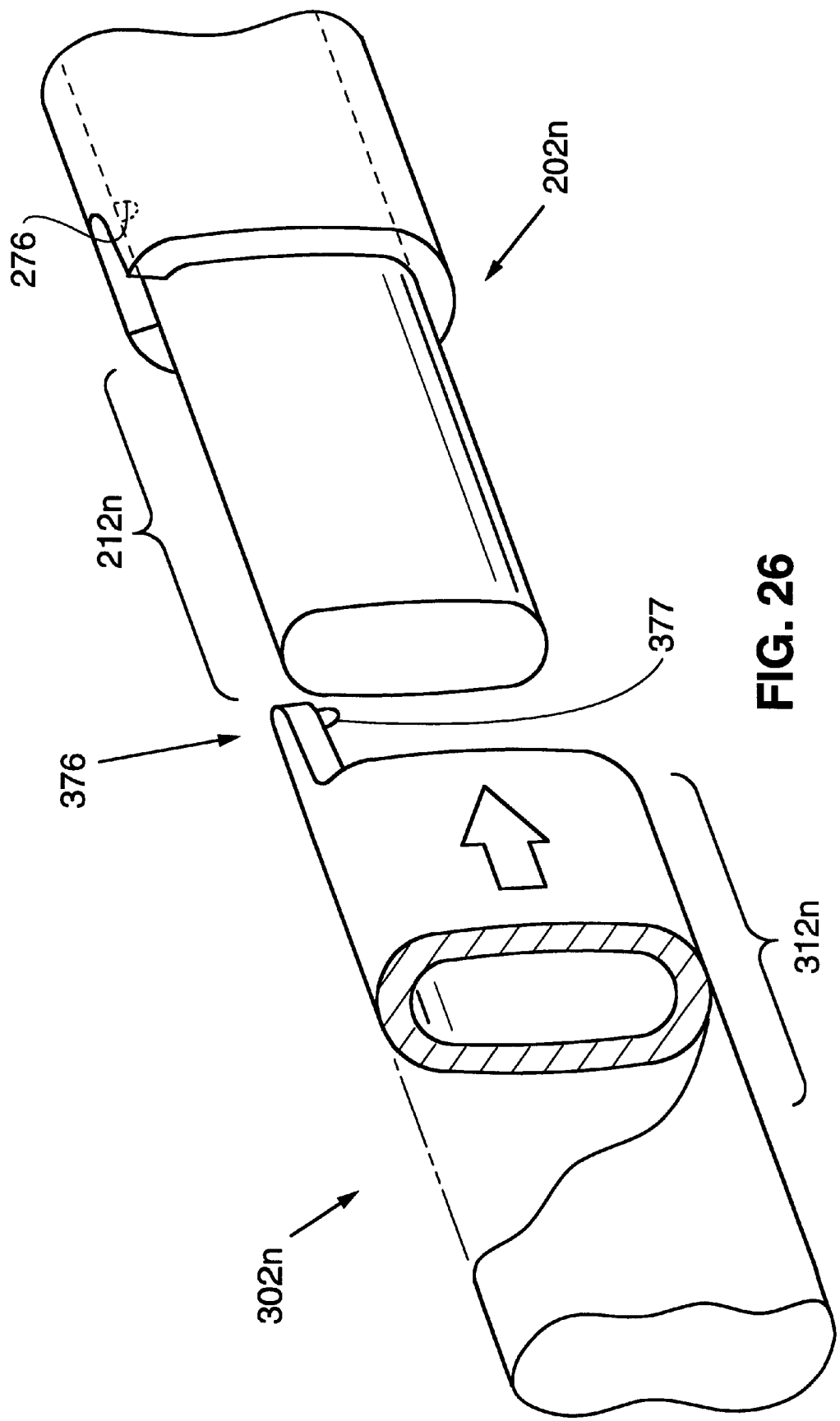
FIG. 26 is an enlarged exploded perspective view, with parts thereof broken away, of a jaw-type surgical clamp according to a fifth embodiment of the present invention.

FIG. 26 shows attachment portions 312n and 212n with generally ellipsoidal cross-sections. The jaw 202n and clamp 302n are secured with a snap latch 376 and a snap notch 276. Latch 376 comprises a resilient arm carrying a detent protrusion 377 for engagement with the notch 276.

Figure 27:
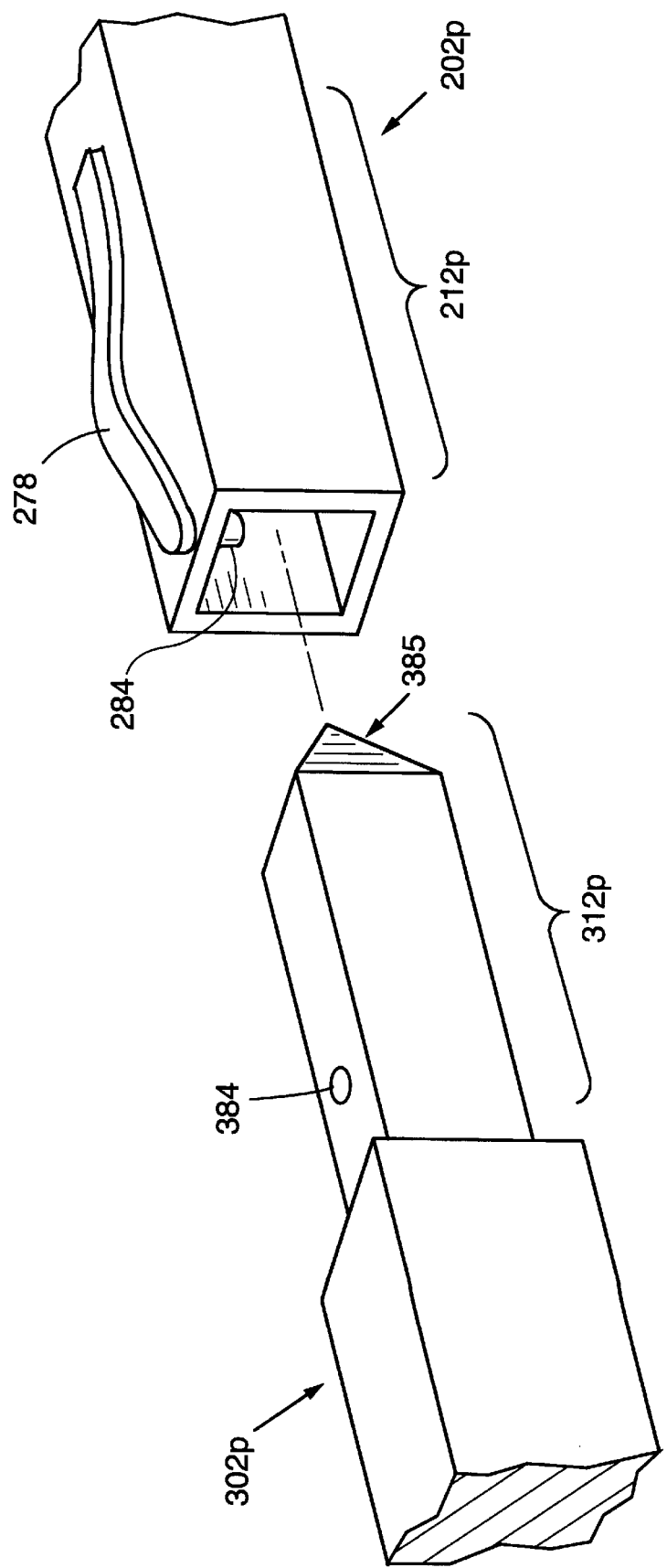
FIG. 27 is an enlarged exploded perspective view, with parts thereof broken away, of a jaw-type surgical clamp according to a sixth embodiment of the present invention.

FIG. 27 shows attachment portions 312p and 212p with generally rectangular cross-sections. The attachment portion 312p of the clamp 302p may include a beveled tip 385 to ease insertion into the attachment portion 212p of the jaw 202p. A flat spring 278 secured to attachment portion 212p carries a locking pin 284 for engagement with a locking pin hole 384 in clamp 302p to releasably secure the clamp 302p and jaw 202p. The telescopic engagement of the jaw 202p in this embodiment is preferably such that the clamp 302p is inserted within the attachment portion 212p. Similar telescopic insertion constructions may be applied to the other embodiments as well.

Figure 28:
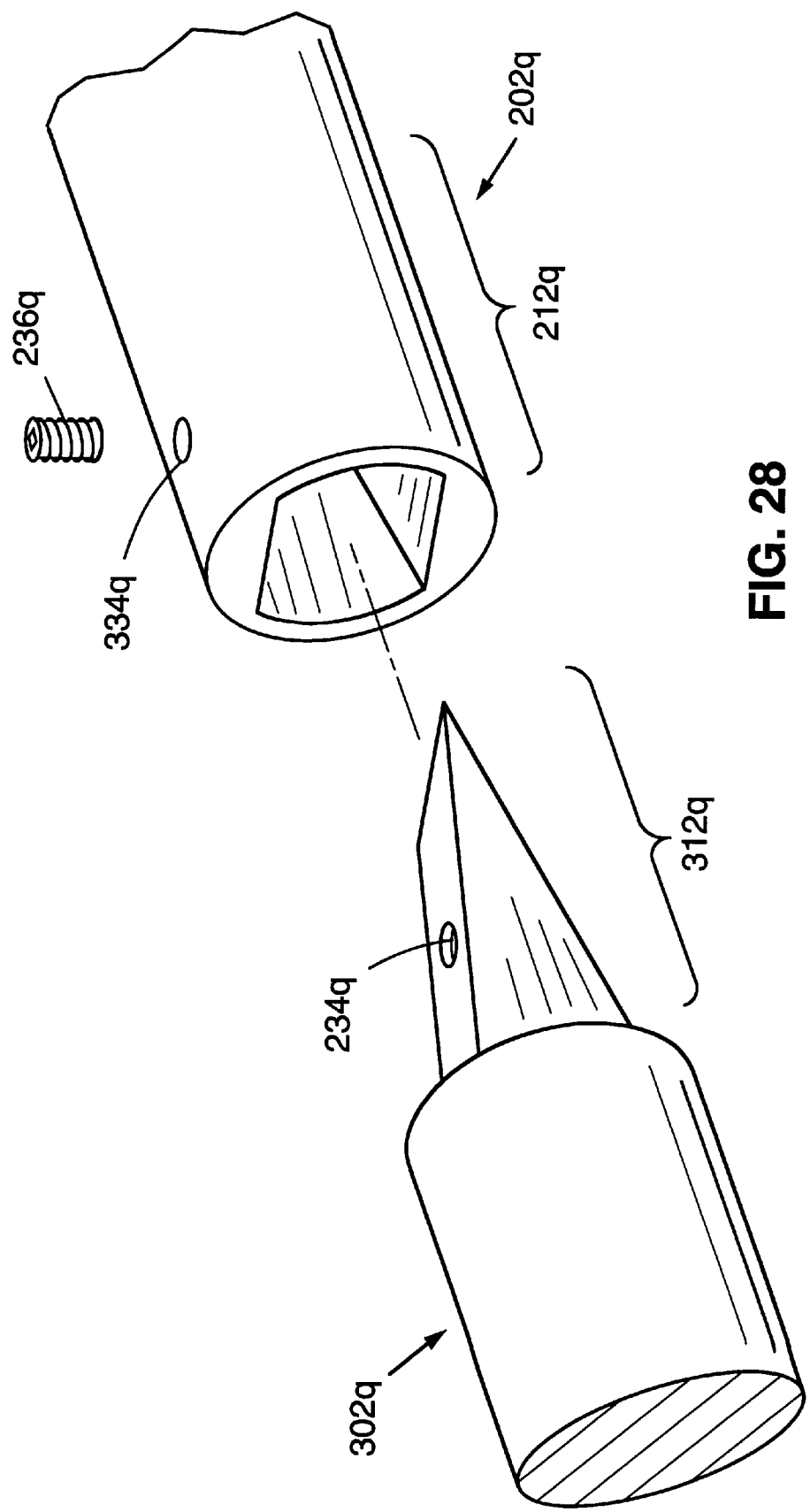
FIG. 28 is an enlarged exploded perspective view, with parts thereof broken away, of a jaw-type surgical clamp according to a seventh embodiment of the present invention.

FIG. 28 shows attachment portions 312q and 212q with generally wedge-shaped cross-sections. The attachment portion 212q includes a hole 334q for insertion of a set screw 236q. The set screw 236q engages a set screw dimple 234q on attachment portion 312q. The dimple 234q may include threads for engagement with the set screw 236q. The set screw 236q may be turned with a screwdriver or hex wrench. In this embodiment the attachment portion 212q telescopically engages the attachment portion 312q.

Figure 29:
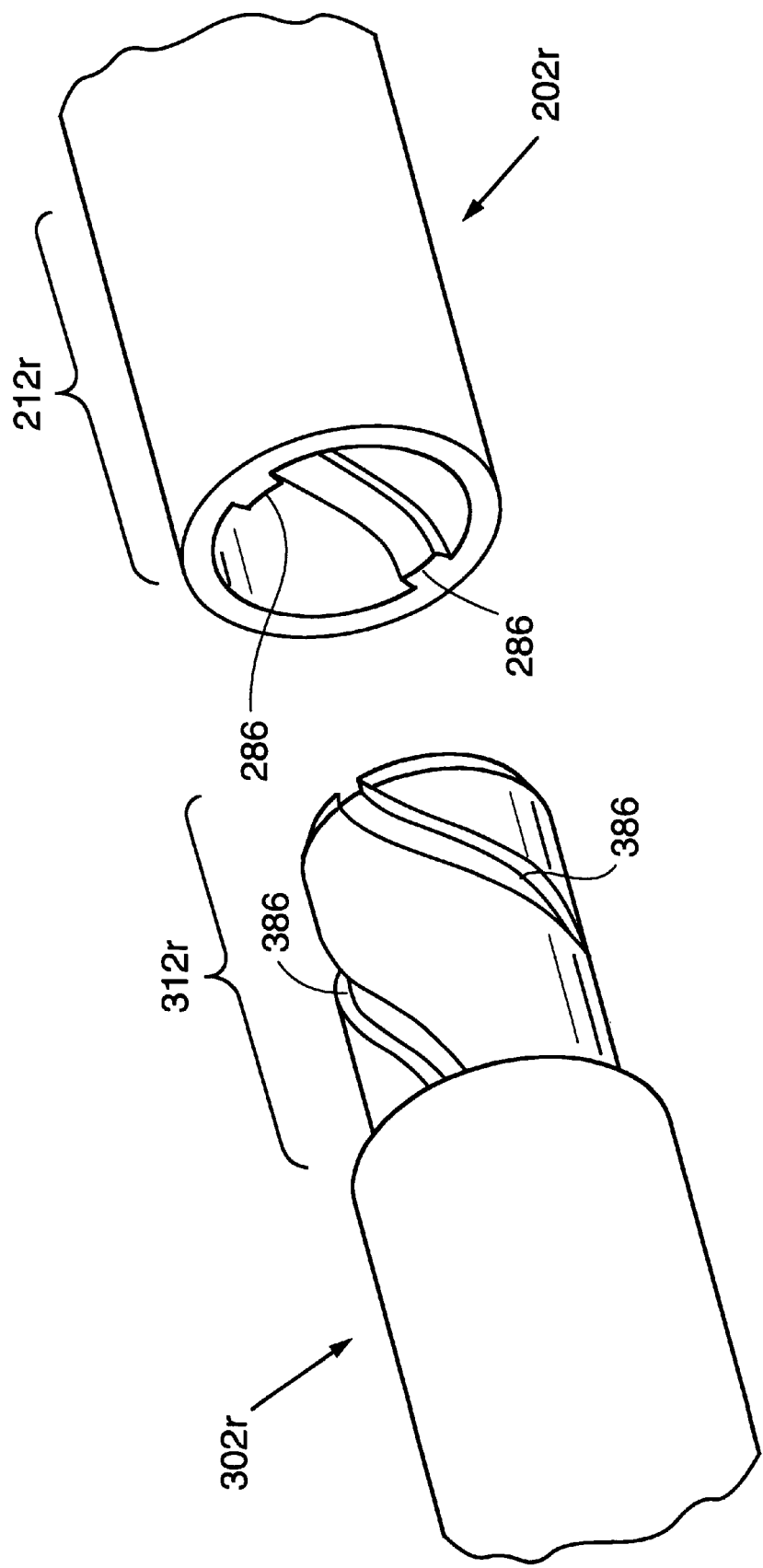
FIG. 29 is an enlarged exploded perspective view, with parts thereof broken away, of a jaw-type surgical clamp according to a eighth embodiment of the present invention.

FIG. 29 shows attachment portions 312r and 212r with generally circular cross-sections. The attachment portion 312r includes one or more helical grooves 386, and the attachment portion 212r includes one or more threads 286. The threads 286 engage the grooves to releasably attach the clamp member 302r to the jaw 202r. Friction keeps the jaw and clamp member attached during operation of the surgical clamp. The grooves 386 and threads 286 are twisted between a ¼ and a ⅓ turn to thread the threads into the grooves to secure the portions 312r and 212r together. The grooves 386 may be equally spaced from one another along the attachment portion 312r as shown, or may be unequally spaced.

Conclusion

From the foregoing detailed description, it is believed that the present invention enables the attainment of the objects initially set forth herein. In particular, the invention provides a surgical clamp wherein the clamp members are removably attachable in order that multiple clamping surfaces and shape configurations are available without requiring a user to purchase multiple surgical clamps.

It should be understood that various alternatives to the embodiments of the invention described herein may be employed in practicing the invention. It is intended that the following claims define the scope of the invention and that structures within the scope of these claims and their equivalents are covered thereby.

What is claimed is:

1. A jaw-type surgical clamp, comprising:
   (a) a pair of jaws, movable toward and away from each other, each of said jaws having an attachment portion and an anti-rotation surface;
   (b) a pair of clamp members removably attachable to said jaws, said clamp members being configured to form clamping surfaces movable toward and away from each other when said clamp members are attached to said jaws, each of said clamp members having:
      (1) an attachment portion configured to telescopically engage the attachment portion of a corresponding one of said jaws; and
      (2) an anti-rotation surface configured for complementary engagement with the anti-rotation surface of the corresponding jaw to prevent rotation between each of said clamp members and the corresponding jaw; and
   (c) mutually engageable structures on said jaws and said clamp members to releasably lock each of said clamp members to the corresponding jaw when engaged therewith;
   and wherein the attachment portion of each of said jaws includes a protruding portion telescopically engageable with the attachment portion of each of said clamp members; and a surrounding portion extending at least partly around said protruding portion, said surrounding portion having edges wherein the anti-rotation surfaces of each of said jaws are defined by said edges.

2. The jaw-type surgical clamp of claim 1, wherein: said protruding portion has a generally cylindrical outer surface.

3. The jaw-type surgical clamp of claim 1, wherein: said surrounding portion occupies less than half of said generally cylindrical outer surface.

4. The jaw-type surgical clamp of claim 1, wherein:
   said surrounding portion occupies more than half of said generally cylindrical outer surface.

5. The jaw-type surgical clamp of claim 1, wherein the attachment portion of each of said clamp members comprises:
   a protruding portion telescopically engageable with the attachment portion of each of said jaws.

6. The jaw-type surgical clamp of claim 1, wherein:
   the attachment portion of said jaws and the attachment portion of said clamp members comprise mutually engageable portions having a generally uniform cross-section.

7. The jaw-type surgical clamp of claim 6, wherein:
   said generally uniform cross-section is a generally circular cross-section.

8. The jaw-type surgical clamp of claim 6, wherein:
   said generally uniform cross-section is a generally triangular cross-section.

9. The jaw-type surgical clamp of claim 6, wherein:
   said generally uniform cross-section is a generally ellipsoidal cross-section.

10. The jaw-type surgical clamp of claim 6, wherein:
    said generally uniform cross-section is a generally rectangular cross-section.

11. The jaw-type surgical clamp of claim 6, wherein:
    the attachment portion of said jaw and the attachment portion of said clamp members comprise mutually engageable portions of a generally wedge-shaped cross-section.

12. The jaw-type surgical clamp of claim 1, wherein said mutually engageable structures comprise:
    a notch on one of said jaw and said clamp member; and
    a detent tab on the other of said jaw and said clamp member configured to engage said notch when said clamp member is attached to said jaw.

13. The jaw-type surgical clamp of claim 1, wherein said mutually engageable structures comprise:
    two notches on one of said jaw and said clamp member; and
    two protruding portions on the other of said jaw and said clamp member configured to engage said two notches when said clamp member is attached to said jaw.

14. The jaw-type surgical clamp of claim 1, wherein said mutually engageable structures comprise:

a snap notch on one of said jaw and said clamp member; and a snap latch on the other of said jaw and said clamp member configured to engage said snap notch and releasably lock said clamp member to said jaw when said clamp member is attached to said jaw.

15. A jaw-type surgical clamp kit, comprising:
(a) a pair of jaws, moveable toward and away from each other, each of said jaws having an attachment portion and an anti-rotation surface;
(b) a plurality of pairs of clamp members removably attachable to said jaws; each pair of said plurality being configured to form clamping surfaces moveable toward and away from each other when each pair is attached to said jaws, wherein a first pair of said plurality differs from a second pair of said plurality such that different clamping surfaces are formed, each of said pair of clamp members having:
  (1) an attachment portion configured to telescopically engage the attachment portion of a corresponding one of said jaws; and
  (2) an anti-rotation surface configured for complementary engagement with the anti-rotation surface of the corresponding jaw to prevent rotation between each of said clamp members and the corresponding jaw; and
(c) mutually engageable structures on said jaws and said clamp members to releasably lock each of said clamp members to the corresponding jaw,
wherein the attachment portion of each of said jaws includes
  a protruding portion telescopically engageable with the attachment portion of each of said clamp members, and
  a surrounding portion extending at least partly around said protruding portion, said surrounding portion having edges, wherein the anti-rotation surfaces of each of said jaws are defined by said edges.

16. A surgical clamp, comprising:
(a) a pair of short arms, movable toward and away from each other, each of said arms having an attachment portion;
(b) clamp members adapted to be removably and rigidly attached to each of said arms to form an elongate extension cantilevered therefrom, said respective clamp members being configured to form clamping surfaces movable toward and away from each other when said clamp members are attached to said arms, each of said clamp members having an attachment portion configured for engagement with the attachment portion of a corresponding one of said arms; and
(c) mutually engageable structures on said arms and said clamp members to releasably lock each of said clamp members to the corresponding arm when engaged therewith,
wherein each of said arms further includes an anti-rotation surface and each of said clamp members further includes an anti-rotation surface configured for complementary engagement with the anti-rotation surface of the corresponding arm to prevent rotation between each clamp member and the corresponding arm,
and wherein the attachment portion of each of said clamp members includes a protruding portion telescopically engageable with the attachment portion of each of said arms and a surrounding portion extending at least partly around said protruding portion, said surrounding portion having edges, wherein the anti-rotation surfaces of each of said clamp members are defined by said edges.

17. The surgical clamp of claim 16, wherein:
the attachment portion of said arms and the attachment portion of said clamp members comprise mutually engagable portions having a generally uniform cross-section.

18. The surgical clamp of claim 16, wherein said mutually engagable structures comprise:
a notch on one of said arm and said clamp member; and
a detent tab on the other of said arm and said clamp member configured to engage said notch when said clamp member is attached to said arm.

19. The surgical clamp of claim 16, wherein said mutually engagable structures comprise:
a snap notch on one of said arm and said clamp member; and
a snap latch on the other of said arm and said clamp member configured to engage said snap notch and releasably lock said clamp member to said arm when said clamp member is attached to said arm.

20. The surgical clamp of claim 16, wherein said mutually engagable structures comprise:
a locking pin hole on one of said arm and said clamp member; and
a flat spring on the other of said arm and said clamp member, said flat spring having a locking pin configured to engage said locking pin hole.

21. The surgical clamp of claim 16, wherein said mutually engagable structures comprise:
a helical groove in one of said arm and said clamp member; and
a helical thread in the other of said arm and said clamp member, said helical thread being configured to engage said helical groove.

22. A surgical clamp, comprising:
(a) a pair of short arms, movable toward and away from each other, each of said arms having an attachment portion; and
(b) clamp members adapted to be removably and rigidly attached to each of said arms to form an elongate extension cantilevered therefrom, said respective clamp members being configured to form clamping surfaces movable toward and away from each other when said clamp members are attached to said arms, each of said clamp members having an attachment portion configured for engagement with the attachment portion of a corresponding one of said arms;
wherein said arms are attached to said clamp members with a semi-permanent bonding substance.

23. The surgical clamp of claim 22, wherein said semi-permanent bonding substance is one of a metal brazing, a silver solder, and a glue.

24. A jaw-type surgical clamp, comprising:
(a) a pair of jaws, movable toward and away from each other, each of said jaws having an attachment portion and an anti-rotation surface;
(b) a pair of clamp members removably attachable to said jaws, said clamp members being configured to form clamping surfaces movable toward and away from each other when said clamp members are attached to said jaws, each of said clamp members having:
  (1) an attachment portion configured to telescopically engage the attachment portion of a corresponding one of said jaws; and (2) an anti-rotation surface configured for complementary engagement with the anti-rotation surface of the corresponding jaw to prevent rotation between each of said clamp members and the corresponding jaw; and (c) mutually engageable structures on said jaws and said clamp members to releasably lock each of said clamp members to the corresponding jaw when engaged therewith;

wherein the attachment portion of said jaws and the attachment portion of said clamp members comprise mutually engageable portions having a generally uniform cross-section, wherein said generally uniform cross-section is a generally rectangular-and-semicircular cross-section.

25. A jaw-type surgical clamp, comprising:

(a) a pair of jaws, movable toward and away from each other, each of said jaws having an attachment portion and an anti-rotation surface;

(b) a pair of clamp members removably attachable to said jaws, said clamp members being configured to form clamping surfaces movable toward and away from each other when said clamp members are attached to said jaws, each of said clamp members having:
  (1) an attachment portion configured to telescopically engage the attachment portion of a corresponding one of said jaws; and
  (2) an anti-rotation surface configured for complementary engagement with the anti-rotation surface of the corresponding jaw to prevent rotation between each of said clamp members and the corresponding jaw; and (c) mutually engageable structures on said jaws and said clamp members to releasably lock each of said clamp members to the corresponding jaw when engaged therewith, wherein said mutually engageable structures include a notch on one of said jaw and said clamp member; and a detent tab on the other of said jaw and said clamp member is configured to engage said notch when said clamp member is attached to said jaw, and further wherein the attachment portion of each of said clamp members has an end, and said detent tab further comprises an elongated detent tab extending beyond the end of the attachment portion of the clamp member.

26. A jaw-type surgical clamp, comprising:

(a) a pair of jaws, movable toward and away from each other, each of said jaws having an attachment portion and an anti-rotation surface;

(b) a pair of clamp members removably attachable to said jaws, said clamp members being configured to form clamping surfaces movable toward and away from each other when said clamp members are attached to said jaws, each of said clamp members having:
  (1) an attachment portion configured to telescopically engage the attachment portion of a corresponding one of said jaws; and
  (2) an anti-rotation surface configured for complementary engagement with the anti-rotation surface of the corresponding jaw to prevent rotation between each of said clamp members and the corresponding jaw; and (c) mutually engageable structures on said jaws and said clamp members to releasably lock each of said clamp members to the corresponding jaw when engaged therewith, wherein said mutually engageable structures include a screw in said jaw configured to move between a recessed position and an extended position in relation to said jaw; and a hole in said clamp member configured to provide access to said screw when said clamp member is attached to said jaw, and wherein said screw may be moved into said extended position to lock said clamp member to said jaw.

27. A jaw-type surgical clamp, comprising:

(a) a pair of jaws, movable toward and away from each other, each of said jaws having an attachment portion and an anti-rotation surface;

(b) a pair of clamp members removably attachable to said jaws, said clamp members being configured to form clamping surfaces movable toward and away from each other when said clamp members are attached to said jaws, each of said clamp members having:
  (1) an attachment portion configured to telescopically engage the attachment portion of a corresponding one of said jaws; and
  (2) an anti-rotation surface configured for complementary engagement with the anti-rotation surface of the corresponding jaw to prevent rotation between each of said clamp members and the corresponding jaw; and (c) mutually engageable structures on said jaws and said clamp members to releasably lock each of said clamp members to the corresponding jaw when engaged therewith, wherein said mutually engageable structures include a crew configure to be inserted into said jaw and configured to move between a recessed position and an extended position in relation to said jaw, and a hole in said clamp member configured to provide access to said screw when said clamp member is attached to said jaw, and wherein said screw may be moved into said recessed position to lock said clamp member to said jaw.

28. A jaw-type surgical clamp, comprising:

(a) a pair of jaws, movable toward and away from each other, each of said jaws having an attachment portion and an anti-rotation surface;

(b) a pair of clamp members removably attachable to said jaws, said clamp members being configured to form clamping surfaces movable toward and away from each other when said clamp members are attached to said jaws, each of said clamp members having:
  (1) an attachment portion configured to telescopically engage the attachment portion of a corresponding one of said jaws; and
  (2) an anti-rotation surface configured for complementary engagement with the anti-rotation surface of the corresponding jaw to prevent rotation between each of said clamp members and the corresponding jaw; and (c) mutually engageable structures on said jaws and said clamp members to releasably lock each of said clamp members to the corresponding jaw when engaged therewith, wherein said mutually engageable structures include a locking pin hole on one of said jaw and said clamp member; and a flat spring on the other of said jaw and said clamp member, said flat spring having a locking pin configured to engage said locking pin hole.

29. A jaw-type surgical clamp, comprising:
(a) a pair of jaws, movable toward and away from each other, each of said jaws having an attachment portion and an anti-rotation surface;
(b) a pair of clamp members removably attachable to said jaws, said clamp members being configured to form clamping surfaces movable toward and away from each other when said clamp members are attached to said jaws, each of said clamp members having:
 (1) an attachment portion configured to telescopically engage the attachment portion of a corresponding one of said jaws; and
 (2) an anti-rotation surface configured for complementary engagement with the anti-rotation surface of the corresponding jaw to prevent rotation between each of said clamp members and the corresponding jaw; and
(c) mutually engageable structures on said jaws and said clamp members to releasably lock each of said clamp members to the corresponding jaw when engaged therewith, wherein said mutually engageable structures include
 a helical groove in one of said jaw said clamp member; and
 a helical thread in the other of said jaw and said clamp member, said helical thread being configured to engage said helical groove.

30. A jaw-type surgical clamp, comprising:
(a) a pair of jaws, movable toward and away from each other, each of said jaws having an attachment portion and an anti-rotation surface;
(b) a pair of clamp members removably attachable to said jaws, said clamp members being configured to form clamping surfaces movable toward and away from each other when said clamp members are attached to said jaws, each of said clamp members having:
 (1) an attachment portion configured to telescopically engage the attachment portion of a corresponding one of said jaws; and
 (2) an anti-rotation surface configured for complementary engagement with the anti-rotation surface of the corresponding jaw to prevent rotation between each of said clamp members and the corresponding jaw; and
(c) mutually engageable structures on said jaws and said clamp members to releasably lock each of said clamp members to the corresponding jaw when engaged therewith; and
(d) a resilient pad interposed in compression between said jaws and said clamp members when engaged to resist relative movement therebetween.

31. The jaw-type surgical clamp of claim 30, wherein the attachment portion of each of said jaws includes an end, wherein said resilient pad comprises:
 a pad located within the attachment portion of each of said clamp members, configured to cushionably seat said end when said clamp members are attached to said jaws.

32. The jaw-type surgical clamp of claim 31, wherein:
the attachment portion of each of said jaws further includes a second end extending beyond said end; and
said pad has a shape of a semi-circular cylinder.

33. A jaw-type surgical clamp, comprising:
(a) a pair of jaws, movable toward and away from each other, each of said jaws having an attachment portion and an anti-rotation surface;
(b) a pair of clamp members removably attachable to said jaws, said clamp members being configured to form clamping surfaces movable toward and away from each other when said clamp members are attached to said jaws, each of said clamp members having:
 (1) an attachment portion configured to telescopically engage the attachment portion of a corresponding one of said jaws; and
 (2) an anti-rotation surface configured for complementary engagement with the anti-rotation surface of the corresponding jaw to prevent rotation between each of said clamp members and the corresponding jaw; and
(c) mutually engageable structures on said jaws and said clamp members to releasably lock each of said clamp members to the corresponding jaw when engaged therewith,
wherein the anti-rotation surface of each of said jaws comprises a groove formed in the attachment portion of each of said jaws; and the anti-rotation surface of each of said clamp members comprises a spline receivable within said groove.

34. A surgical clamp, comprising:
(a) a pair of short arms, movable toward and away from each other, each of said arms having an attachment portion;
(b) clamp members adapted to be removably and rigidly attached to each of said arms to form an elongate extension cantilevered therefrom, said respective clamp members being configured to form clamping surfaces movable toward and away from each other when said clamp members are attached to said arms, each of said clamp members having an attachment portion configured for engagement with the attachment portion of a corresponding one of said arms; and
(c) mutually engageable structures on said arms and said clamp members to releasably lock each of said clamp members to the corresponding arm when engaged therewith, wherein said mutually engageable structures include
 a screw in said arm configured to move between a recessed position and an extended position in relation to said arm; and
 a hole in said clamp member configured to provide access to said screw when said clamp member is attached to said arm, wherein said screw may be moved into said extended position to lock said clamp member to said arm.

35. A surgical clamp, comprising:
(a) a pair of short arms, movable toward and away from each other, each of said arms having an attachment portion;
(b) clamp members adapted to be removably and rigidly attached to each of said arms to form an elongate extension cantilevered therefrom, said respective clamp members being configured to form clamping surfaces movable toward and away from each other when said clamp members are attached to said arms, each of said clamp members having an attachment portion configured for engagement with the attachment portion of a corresponding one of said arms; and
(c) mutually engageable structures on said arms and said clamp members to releasably lock each of said clamp members to the corresponding arm when engaged therewith, wherein said mutually engageable structures include a screw configured to be inserted into said arm and configured to move between a recessed position and an extended position in relation to said arm; and a hole in said clamp member configured to receive said screw when said clamp member is attached to said arm, wherein said screw may be moved into said recessed position to lock said clamp member to said arm.

* * * * *